United States Patent [19]

Miesel

[11] 4,160,834

[45] Jul. 10, 1979

[54] 1-(SUBSTITUTED BENZOYL)-3-(SUBSTITUTED PYRAZINYL)UREAS

[75] Inventor: John L. Miesel, Indianapolis, Ind.

[73] Assignee: Eli Lilly and Company, Indianapolis, Ind.

[21] Appl. No.: 861,733

[22] Filed: Dec. 19, 1977

Related U.S. Application Data

[63] Continuation-in-part of Ser. No. 775,813, Mar. 9, 1977, abandoned, which is a continuation-in-part of Ser. No. 595,904, Jul. 14, 1975, abandoned, which is a continuation-in-part of Ser. No. 507,492, Sep. 19, 1974, abandoned.

[51] Int. Cl.² .................. A61K 31/495; C07D 241/20
[52] U.S. Cl. ..................... 424/250; 544/336; 544/408; 544/409
[58] Field of Search .............. 260/250 BN; 424/250; 544/336, 408, 409

[56] References Cited

U.S. PATENT DOCUMENTS

| | | | |
|---|---|---|---|
| 3,940,392 | 2/1976 | Johnston | 260/250 BN |
| 4,083,977 | 4/1978 | Miesel | 544/356 |

*Primary Examiner*—Jose Tovar
*Attorney, Agent, or Firm*—Dwight E. Morrison; Arthur R. Whale

[57] ABSTRACT

Novel 1-(substituted benzoyl)-3-(substituted pyrazinyl)ureas, active as insecticides, and methods for their use as insecticides.

40 Claims, No Drawings

1-(SUBSTITUTED BENZOYL)-3-(SUBSTITUTED PYRAZINYL)UREAS

CROSS-REFERENCE

This application is a continuation-in-part of my copending application Ser. No. 775,813, filed Mar. 9, 1977, now abandoned which was a continuation-in-part of application Ser. No. 595,904, filed July 14, 1975, now abandoned, which was a continuation-in-part of my then copending application Ser. No. 507,492, filed Sept. 19, 1974, now abandoned.

BACKGROUND OF THE INVENTION

1. Field of the Invention

The control of insects is of vital importance in the increasingly populous world today. It is well known that insects such as those belonging to the orders of Lepidoptera, Coleoptera, Diptera, Homoptera, Hemiptera and Orthoptera, at the larval stage, cause extensive damage to many crops, for example, food crops and fibrous crops. Control of such insects contributes to the well-being of mankind by increasing the supplies of food and of the fibrous materials useful in the production of clothing.

2. Description of the Prior Art

In the prior art, Wellinga et al., U.S. Pat. No. 3,748,356 (July 24, 1973), describe a series of substituted benzoylureas which are taught as having strong insecticidal activity. The Wellinga et al. compounds are generally 1-(2,6-dichlorobenzoyl)-3-(substituted phenyl)ureas, but also include several 1-(2,6-dichlorobenzoyl)-3-(substituted pyridyl)ureas.

Also in the prior art, Wellinga et al., U.S. Pat. No. 3,989,842 (Nov. 2, 1976), teach and claim insecticidal compositions and a method of controlling insects in agriculture and horticulture utilizing certain N-(2,6-dihalobenzoyl)-N'-(substituted phenyl)urea compounds as the active ingredient, as well as several N-(2,6-dichlorobenzoyl)-N'-(substituted pyridyl)ureas.

Other N-(2,6-dihalobenzoyl)-N'-(substituted phenyl)-urea compounds are disclosed and claimed in Wellinga et al., U.S. Pat. No. 3,933,908 (Jan. 20, 1976), which compounds are disclosed as having insecticidal activity.

A number of prior art references discuss the insecticidal activity of 1-(2,6-dichlorobenzoyl)-3-(3,4-dichlorophenyl)urea. See Van Daalen et al., Die Naturwissenschaften 59, 312–313 (1972); Post et al., ibid. 60, 431–432 (1973); Mulder et al., Pestic. Sci. 4, 737–745 (1973).

Studies in the inhibition of the development of mosquitoes and houseflies, and of the control of alfalfa weevil, by the action of 1-(4-chlorophenyl)-3-(2,6-difluorobenzoyl)urea are reported by Jakob, J. Med. Ent. 10, 452–455 (1973), and Neal, Jr., J. Econ. Ent., 67, 300–301 (1974), respectively.

Further in the prior art, U.S. Pat. No. 4,005,223 (Jan. 25, 1977), and British Pat. No. 1,460,418, teach 1-benzoyl-3-(phenoxyphenyl)ureas as insecticides with low mammalian and plant toxicity.

None of the prior art teaches compounds of the structure disclosed in the present application.

SUMMARY OF THE INVENTION

This invention is directed to novel 1-(substituted benzoyl)-3-(substituted pyrazinyl)ureas having insecticidal activity, and to methods of use of the novel compounds.

DESCRIPTION OF THE PREFERRED EMBODIMENT

This invention relates to novel 1-(substituted benzoyl)-3-(substituted pyrazinyl)ureas off the formula

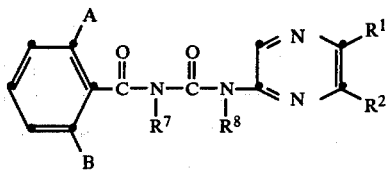

wherein

A and B are the same or different, and are halo, methyl, or trifluoromethyl;

$R^1$, when taken separately, is hydrogen, halo, $C_1$–$C_6$ alkyl, $C_3$–$C_6$ cycloalkyl, halo($C_1$–$C_4$)alkyl, nitro, cyano,

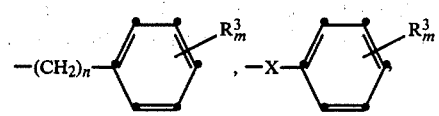

or naphthyl;

$R^2$, when taken separately, is hydrogen, halo, methyl, ethyl, cyano, or halo($C_1$–$C_2$)alkyl;

With the limitation that $R^1$ and $R^2$ may not both be hydrogen at the same time;

$R^3$ is halo, halo($C_1$–$C_4$)alkyl, $C_1$–$C_6$ alkyl, $C_1$–$C_4$ alkoxy, $C_1$–$C_4$ alkylthio, $C_1$–$C_4$ alkylsulfonyl, nitro, cyano, or phenyl;

m is 0, 1, 2, or 3;

n is 0 or 1;

X is —O—, —S—, or

$R^1$ and $R^2$, when taken together with the pyrazine ring to which they are attached, form a benzopyrazine (quinoxaline) of the formula:

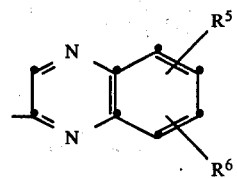

wherein $R^5$ and $R^6$ are the same or different, and are hydrogen, halo, $C_1$–$C_6$ alkyl, $C_3$–$C_6$ cycloalkyl, nitro, cyano, or halo($C_1$–$C_4$)alkyl;

$R^7$ and $R^8$, when taken separately, are the same or different, and are hydrogen, $C_1$–$C_4$ alkanoyl, or $C_1$–$C_3$ alkoxycarbonyl.

In another embodiment of this invention, $R^7$ and $R^8$, when taken together with the group

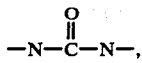

form ring systems represented by the following formulae

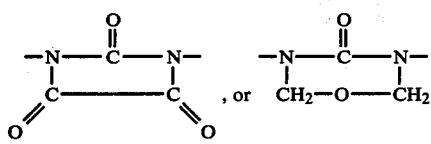

while the values of $R^1$-$R^6$, inclusive, m, n, and X are the same as set forth hereinbefore.

One preferred group of compounds of this invention are those compounds coming within the scope of the above generic formula wherein A and B are the same or different, and are halo, methyl, or trifluoromethyl;

$R^1$, when taken separately, is hydrogen, halo, $C_1$-$C_6$ alkyl, $C_3$-$C_6$ cycloalkyl, halo($C_1$-$C_4$)alkyl, nitro, cyano,

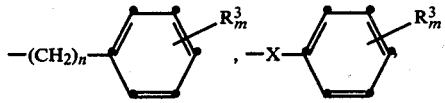

or naphthyl;

$R^2$, when taken separately, is hydrogen, halo, methyl, ethyl, cyano, or halo($C_1$-$C_2$)alkyl;

with the limitation that $R^1$ and $R^2$ may not both be hydrogen at the same time;

$R^3$ is halo, $C_1$-$C_6$ alkyl, halo($C_1$-$C_4$)alkyl, $C_1$-$C_4$ alkoxy, $C_1$-$C_4$ alkylthio, $C_1$-$C_4$ alkylsulfonyl, nitro, cyano, or phenyl;

m is 0, 1, 2, or 3;
n is 0 or 1;
X is —O—, —S—, or

$R^1$ and $R^2$, when taken together with the pyrazine ring to which they are attached, form a benzopyrazine (quinoxaoline) of the formula

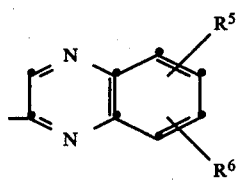

wherein $R^5$ and $R^6$ are the same or different, and are hydrogen, halo, $C_1$-$C_6$ alkyl, $C_3$-$C_6$ cycloalkyl, nitro, cyano, or halo($C_1$-$C_4$)alkyl;

$R^7$ and $R^8$, when taken separately, are the same or different, and are hydrogen, $C_1$-$C_4$ alkanoyl, or $C_1$-$C_3$ alkoxycarbonyl.

Another group of preferred compounds of this invention are those compounds coming within the scope of the above generic formula wherein A and B are the same and are halo or methyl;

$R^1$, when taken separately, is hydrogen, halo, $C_1$-$C_6$ alkyl, halo($C_1$-$C_4$)alkyl, cyano,

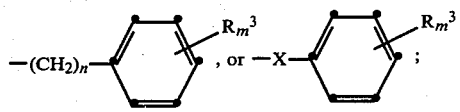

$R^2$, when taken separately, is hydrogen, halo, methyl, ethyl, cyano, or halo($C_1$-$C_2$)alkyl;

with the limitation that $R^1$ and $R^2$ may not both be hydrogen at the same time;

$R^3$ is halo, $C_1$-$C_6$ alkyl, $C_1$-$C_4$ alkoxy, or halo($C_1$-$C_4$)alkyl;

m is 0, 1, or 2;
n is 0 or 1;
X is —O—;

$R^1$ and $R^2$, when taken together with the pyrazine ring to which they are attached, form a benzopyrazine (quinoxaline) of the formula:

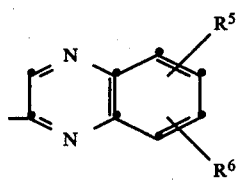

wherein $R^5$ and $R^6$ are the same or different, and are hydrogen, halo, or halo($C_1$-$C_4$)alkyl; and $R^7$ and $R^8$, when taken separately, are the same or different, and are hydrogen, $C_1$-$C_4$ alkanoyl, or $C_1$-$C_3$ alkoxycarbonyl.

The most preferred compounds of this invention are those compounds coming within the scope of the above generic formula wherein A and B are the same and are halo or methyl;

$R^1$, when taken separately, is hydrogen, halo, $C_1$-$C_6$ alkyl, halo($C_1$-$C_4$)alkyl, cyano,

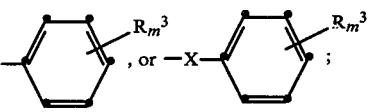

$R^2$, when taken separately, is hydrogen, halo, methyl, ethyl, cyano, or halo($C_1$-$C_2$)alkyl;

with the limitation that $R^1$ and $R^2$ may not both be hydrogen at the same time;

$R^3$ is halo, $C_1$-$C_6$ alkyl, $C_1$-$C_4$ alkoxy, or halo($C_1$-$C_4$)alkyl;

m is 0, 1, or 2;
n is 0 or 1;
X is —O—;

$R^7$ and $R^8$, when taken separately, are the same or different, and are hydrogen, $C_1$-$C_4$ alkanoyl, or $C_1$-$C_3$ alkoxycarbonyl.

The compounds of choice are those coming within the scope of the generic formula, supra, wherein A and B are the same, and are halo;

$R^1$ is hydrogen, bromo, chloro, halo($C_1$–$C_4$)alkyl, or

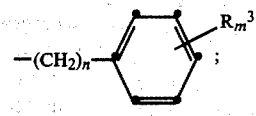

$R^2$ is hydrogen, methyl, ethyl, or halo($C_1$–$C_2$)alkyl;
$R^3$ is halo, $C_1$–$C_6$alkyl, or halo($C_1$–$C_4$)alkyl;
m is 0, 1, or 2; n is 0; and
$R^7$ and $R^8$ are hydrogen.

In the generic formula above, halo refers to fluoro, chloro, and bromo.

$C_1$–$C_6$ Alkyl represents straight- or branched-chain saturated alkyl including methyl, ethyl, n-propyl, isopropyl, n-butyl, sec.-butyl, t-butyl, isobutyl, n-amyl, isoamyl, sec.-amyl, t-amyl, n-hexyl, isohexyl, t-hexyl and the like.

$C_3$–$C_6$ Cycloalkyl represents saturated cycloalkyl having from 3 to 6 carbon atoms in the ring and is exemplified by cyclopropyl, cyclobutyl, cyclopentyl and cyclohexyl.

Halo($C_1$–$C_4$)alkyl represents a series of halogenated straight or branched-chain alkyl such as trifluoromethyl, 1,1-difluoroethyl, pentafluoroethyl, 1,1,2,2,-tetrafluoroethyl, chlorodifluoromethyl, trichloromethyl, 2-bromoethyl, 3-bromopropyl, 4-bromobutyl, 3-chloropropyl and 3-chlorobutyl.

$C_2$–$C_4$ Alkanoyl refers to acetyl, propionyl and butyryl.

$C_1$–$C_3$ Alkoxycarbonyl refers to methoxycarbonyl, ethoxycarbonyl, propoxycarbonyl, and isopropoxycarbonyl.

Halo($C_1$–$C_2$)alkyl refers to a series of halogenated alkyl such as trifluoromethyl, 1,1-difluoroethyl, pentafluoroethyl, 1,1,2,2-tetrafluoroethyl, chlorodifluoromethyl, trichloromethyl and 2-bromoethyl.

$C_1$–$c_4$ Alkoxy represents methoxy, ethoxy, propoxy, isopropoxy, n-butoxy, sec.-butoxy, and t-butoxy.

$C_1$–$C_4$ Alkylthio represents methylthio, ethylthio, n-propylthio, isopropylthio, n-butylthio, sec.-butylthio, isobutylthio, and t-butylthio.

$C_1$–$C_4$ Alkylsulfonyl represents methylsulfonyl, ethylsulfonyl, n-propylsulfonyl, isopropylsulfonyl, butylsulfonyl, isobutylsulfonyl, sec.-butylsulfonyl, and t-butylsulfonyl.

Novel compounds coming within the scope of the generic formula above include, but are not limited to the following:

1-(2,6-Dimethylbenzoyl)-3-(6-ethyl-2-pyrazinyl)-urea
1-(2,6-Dimethylbenzoyl)-3-(5-phenylsulfonyl-2-pyrazinyl)urea
1-(6-Cyclohexyl-2-quinoxalinyl)-3-(2,6-dimethylbenzoyl)urea
1-(5-Cyano-2-quinoxalinyl)-3-(2,6-dimethylbenzoyl)urea
1-(6-t-Butyl-2-quinoxalinyl)-3-(2,6-dimethylbenzoyl)urea
1-(2,6-Dimethylbenzoyl)-3-(6-nitro-2-quinoxalinyl)urea
1-(5-Chloro-2-pyrazinyl)-3-(2,6-dichlorobenzoyl)-parabanic acid
1-(5-Chloro-2-pyrazinyl)-3-(2,6-dibromobenzoyl)-urea
1-(5-Chloro-2-pyrazinyl)-3-[2,6-bis(trifluoromethyl)benzoyl]urea
1-(2,6-Dibromobenzoyl)-3-(5,6-dimethyl-2-pyrazinyl)urea
1-(6,7-Dibromo-2-quinoxalinyl)-3-(2,6-dichlorobenzoyl)urea
1-(2,6-Dichlorobenzoyl)-3-[(5-n-propyl-6-methyl)2-pyrazinyl]urea
1-(2,6-Dibromobenzoyl)-3-(5-phenoxy-2-pyrazinyl)urea
1-(2,6-Difluorobenzoyl)-3-(6-ethyl-2-pyrazinyl)-urea
1-(5-Cyclopropyl-2-pyrazinyl)-3-(2,6-Dichlorobenzoyl)urea
1-(2,6-Dichlorobenzoyl)-3-(6-methyl-2-pyrazinyl)-urea
1-(2,6-Difluorobenzoyl)-3-(5-naphthyl-2-pyrazinyl)-urea
1-(2,6-Dibromobenzoyl)-3-(6-ethyl-2-pyrazinyl)-urea
1-(2,6-Difluorobenzoyl)-3-(5-isopropyl-2-pyrazinyl)urea
1-(6-Cyano-2-pyrazinyl)-3-(2,6-difluorobenzoyl)-urea
1-(5-Cyano-2-pyrazinyl)-3-(2,6-dibromobenzoyl)-urea
1-(5-Bromo-2-pyrazinyl)-3-(2,6-dichlorobenzoyl)-urea
1-(2,6-Dichlorobenzoyl)-3-[5-(2-trifluoromethyl phenyl)-2-pyrazinyl]urea
1-(2,6-Dibromobenzoyl)-3-[6-methyl-5-(4-trifluoromethylphenyl)-2-pyrazinyl]urea
3-(5-Chloro-2-pyrazinyl)-5-(2,6-dichlorobenzoyl)-2,3,5,6-tetrahydro-1,3,5-oxadizin-4-one
1-[5-(2-Bromoethyl)-2-pyrazinyl]-3-(2,6-dichlorobenzoyl)urea
1-(2,6-Dichlorobenzoyl)-3-(6-trifluoromethyl-2-quinoxalinyl)urea
1-(2,6-Difluorobenzoyl)-3-(7-ethyl-2-quinoxalinyl)-urea
1-(6-Chloro-2-pyrazinyl)-3-(2,6-dichlorobenzoyl)-3-ethoxycarbonylurea
1-[5-(2-Chloroethyl)-2-pyrazinyl]-3-(2,6-dibromobenzoyl)urea
1-(2,6-Dimethylbenzoyl)-3-(5-naphthyl-2-pyrazinyl)-urea
1-(2,6-Dimethylbenzoyl)-3-(5-phenylthio-2-pyrazinyl)urea
1-(5-cyclopentyl-2-pyrazinyl)-3-(2,6-dichlorobenzoyl)urea
1-(2,6-Difluorobenzoyl)-3-[5-(2,4-xylyl)-6-methyl-2-pyrazinyl]urea
1-(2,6-Dichlorobenzoyl)-3-[5-(4-chlorophenylsulfonyl)-2-pyrazinyl]urea
1-(2,6-Dibromobenzoyl)-3-[5-(3,4-xylylsulfonyl)-2-pyrazinyl]urea
1-[5-(3,4-dichlorophenylsulfonyl)-2-pyrazinyl]-3-(2,6-dimethylbenzoyl)urea
1-(2,6-Dichlorobenzoyl)-3-[5-(2,4-xylyloxy)-2-pyrazinyl]urea
1-(2,6-Dichlorobenzoyl)-3-[5-(3,4-xylylthio)-6-methyl-2-pyrazinyl]urea
1-(2,6-Dichlorobenzoyl)-3-[5-(3,4-dichlorophenylthio)-2-pyrazinyl]urea
1-(2,6-Dichlorobenzoyl)-3-[5-(4-trifluoromethylphenylthio)-6-ethyl-2-pyrazinyl]urea
1-[2,6-Bis(trifluoromethyl)benzoyl]-3-[5-p-tolylthio)-6-methyl-2-pyrazinyl]urea
1-(2,6-Dichlorobenzoyl)-3-[5-(2-trifluoromethylphenoxy)-2-pyrazinyl]urea
1-[5-(4-Anisyloxy)-2-pyrazinyl]-3-(2,6-dichlorobenzoyl)urea 1-[5-(4-Chlorobenzyl)-6-ethyl-2-pyrazinyl]-3-(2,6-dimethylbenzoyl)urea 1-(2,6-Dimethylbenzoyl)-3-[5-(4-methylbenzyl)6-methyl-2-pyrazinyl]urea 1-(2,6-Dichlorobenzoyl)-3-[5-(3-trifluoromethylbenzyl)-2-pyrazinyl]urea 1-(2,6-Dichlorobenzoyl)-3-[5-(2,4-dimethylbenzyl)-6-bromo-2-pyrazinyl]urea 1-(2,6-Dichlorobenzoyl)-3-[5-(4-trifluoromethylphenoxy)-6-methyl-2-pyrazinyl]urea 1-(2,6-Dimethylbenzoyl)-3-[5-(3,4-xylyloxy)2-pyrazinyl]urea 1-(2,6-Dichlorobenzoyl)-3-[5-(2-trifluoromethylphenylsulfonyl)-2-pyrazinyl]urea 1-(2,6-Dichlorobenzoyl)-3-[5-(3,4-dichlorophenylsulfonyl)-6-chloro-2-pyrazinyl]urea 1-(2,6-Dimethylbenzoyl)-3-[5-(p-tolylsulfonyl)-6-cyano-2-pyrazinyl]urea 1-[5-(4-Bromobenzyl)-6-methyl-2-pyrazinyl]-3-(2,6-dichlorobenzoyl)urea 1-(2,6-Dichlorobenzoyl)-3-[5-(3-chlorobenzyl)-6-(2-bromoethyl)-2-pyrazinyl]urea 1-(2,6-Dichlorobenzoyl)-3-[5-(4-methylsulfonylphenyl)-6-methyl-2-pyrazinyl]urea 1-[5-(3-Ethylsulfonylphenyl)-2-pyrazinyl]-3-[2,6-bis(trifluoromethyl)benzoyl]urea 1-[2,6-Bis(trifluoromethyl)benzoyl]-3-[5-(3-trifluoromethylphenylthio)-6-methyl-2-pyrazinyl]urea 1-[5-(3-Bromophenoxy)-2-pyrazinyl]-3-(2,6-dimethylbenzoyl)urea 1-(2,6-Dimethylbenzoyl)-3-[5-(3-nitrophenyl)-6-ethyl-2-pyrazinyl]urea 1-(6-Cyano-2-quinoxalinyl)-3-(2,6-dimethylbenzoyl)urea 1-(2,6-Dichlorobenzoyl)-3-(6-nitro-2-quinoxalinyl)urea 1-[5-(3-Anisyloxy)-2-pyrazinyl]-3-(2,6-dichlorobenzoyl)urea 1-(6-Ethyl-2-quinoxalinyl)-3-(2,6-dimethylbenzoyl)urea 1-(7-Ethyl-2-quinoxalinyl)-3-[2,6-bis(trifluoromethyl)benzoyl]urea 1-[5-(3-Cyanophenyl)-2-pyrazinyl]-3-(2,6-dimethylbenzoyl)urea 1-(2,6-Dichlorobenzoyl)-3-[5-(4-phenyl)phenyl-2-pyrazinyl]urea 1-(2,6-Dichlorobenzoyl)-3-[5-(2,4,6-trimethyl)-phenyl-2-pyrazinyl]urea 1-(2,6-Dibromobenzoyl)-3-(5-nitro-2-pyrazinyl)-urea 1-(5-Benzyl-2-pyrazinyl)-3-(2,6-dibromobenzoyl)urea 1-(5-Cyano-2-pyrazinyl)-3-(2,6-dichlorobenzoyl)urea 1-(6-Bromo-2-pyrazinyl)-3-(2,6-dichlorobenzoyl)urea 1-(6-Cyclohexyl-2-quinoxalinyl)-3-(2,6-dichlorobenzoyl)urea 1-Acetyl-1-(2,6-dibromobenzoyl)-3-(6-chloro-2-quinoxalinyl)urea 1-(2,6-Difluorobenzoyl)-3-[6-hexyl-2-quinoxalinyl]urea 1-(2,6-Dichlorobenzoyl)-3-(6-ethyl-2-quinoxalinyl)urea 1-(2,6-Difluorobenzoyl)-3-[5-(1,1,2,2-tetrafluoroethyl)-2-pyrazinyl]urea 1-(2,6-Dichlorobenzoyl)-3-[5-(pentafluoroethyl)-6-methyl-2-pyrazinyl]urea 1-(2,6-Dichlorobenzoyl)-3-[5-methyl-6-(pentafluoroethyl)-2-pyrazinyl]urea 1-(2,6-Difluorobenzoyl)-3-[5-ethyl-6-(1,1,2,2-tetrafluoroethyl)-2-pyrazinyl]urea.

The novel compounds of this invention have been found to be active as insecticides by their action in interfering with the growth of sensitive insects. The compounds appear to interfere with the molting process of the insects and thus cause death. The compounds have been found to act on the insects as a result of the insects ingesting the compounds, e.g., by ingesting the leaves and foliage treated with the active compounds, or ingesting any other part of their normal habitat, e.g., water, manure, and the like, to which the active compounds have been applied. Because of this property, the compounds are useful in a novel method of controlling insects at the larval stage.

The novel compounds of this invention are prepared by procedures known to the art.

Thus, in general, the novel compounds are prepared by allowing a 2,6-disubstituted-benzoylisocyanate to react with an aminopyrazine or an aminoquinoxaline, to yield the desired 1-(2,6-disubstituted benzoyl)-3-(substituted 2-pyrazinyl)urea.

Some of the starting materials are commercially available, others are prepared by utilizing procedures which are known to the art.

The 2,6-disubstituted-benzoylisocyanates are readily prepared from, for instance, 2,6-disubstituted-benzamides, following the general procedure of Speziale et al., J. Org. Chem. 27, 3742 (1962).

One of the intermediates, 2-amino-5-chloropyrazine is prepared following the general procedure of Palamidessi and Bernardi, J. Org. Chem. 29, 2491 (1964), wherein methyl 2-amino-3-pyrazinylcarboxylate is allowed to react with chlorine in acetic acid to yield methyl 2-amino-5-chloro-3-pyrazinylcarboxylate. This ester is hydrolyzed with aqueous sodium hydroxide to yield 2-amino-3-carboxy-5-chloropyrazine, which is then heated in tetrahydronaphthalene and decarboxylated to yield the desired 2-amino-5-chloropyrazine.

Another intermediate, 2-amino-5,6-dichloropyrazine, is prepared by allowing 2-amino-6-chloropyrazine to react with N-chlorosuccinimide in chloroform to yield a mixture of 2-amino-5,6-dichloropyrazine, 2-amino-3,6-dichloropyrazine, and 2-amino-3,5,6-trichloropyrazine. The mixture is then separated by column chromatography and the desired 2-amino-5,6-dichloropyrazine is obtained.

The 2-amino-5-phenylpyrazine necessary for this work is prepared according to the procedure of Lont et al., Rec. Trav. Chim. 92, 455 (1973), and references therein.

Other 2-amino-5(or 6)-substituted pyrazines useful in preparing the novel final compounds of this invention are prepared utilizing oxime derivatives of certain ketones. Thus, 2-oxopropanal 1-oxime and 2-oxobutanal 1-oxime are prepared from ethyl acetoacetate and ethyl propioacetate, respectively, following the procedure of Meyer et al., Chem. Ber. 11, 695 (1878). Other oxime intermediates are prepared from such ketones as acetophenone, 4-trifluoromethylacetophenone, 4-fluoroacetophenone, 2,4-dimethylacetophenone, 4-n-butylacetophenone, 4-chloroacetophenone, m-trifluoromethylacetophenone, and benzyl methyl ketone, following the general procedure of Claisen et al., Chem. Ber. 20, 2194 (1887). Still other oxime intermediates are prepared from ketones such as 4-methoxypropiophenone, 4-trifluoromethylpropiophenone, 4-fluoropropiophenone, 4-n-butylpropiophenone, 4-bromobutyrophenone, 4-bromopropiophenone, and methyl neopentyl ketone, following the general procedure of Hartung et al., J. Am. Chem. Soc. 51, 2262 (1929).

Yet another oxime intermediate is prepared from t-butyl methyl ketone, which is first transformed into t-butylglyoxal using the procedure of Fuson et al., J. Am. Chem. Soc. 61, 1938 (1939). The t-butylglyoxal, in aqueous solution at pH 4–5, is allowed to react with acetone oxime (commercially available) at about room temperature for about two days. The reaction product mixture is worked up by extracting it with ether, and the t-butylglyoxal oxime is isolated from the ether extract as colorless needles having a melting point of about 50°–52° C.

The intermediate 2-amino-5-methylpyrazine is prepared stepwise, starting with 2-oxopropanal 1-oxime. This oxime is allowed to react with aminomalononitrile tosylate [prepared by the method of Ferris et al., J. Am. Chem. Soc. 88, 3829 (1966)], to yield 2-amino-3-cyano-5-methylpyrazine 1-oxide. The pyrazine 1-oxide prepared in this manner is allowed to react with phosphorous trichloride to yield 2-amino-3-cyano-5-methylpyrazine. This 2-amino-3-cyano-5-methylpyrazine is hydrolyzed with aqueous sodium hydroxide to yield 2-amino-3-carboxy-5-methylpyrazine, which, when heated in tetrahydronaphthalene, is decarboxylated to yield the desired 2-amino-5-methylpyrazine.

Following the same general procedure set forth in the preceding paragraph, and starting with 2-oxobutanal 1-oxime, there is obtained 2-amino-5-ethylpyrazine.

Another intermediate pyrazine compound, 2-amino-5-(4-bromophenyl)-6-methylpyrazine is synthesized starting with 1-(4-bromophenyl)-1,2-propanedione 2-oxime, which oxime is obtained by the same general procedure of Hartung et al., supra. This oxime is allowed to react with aminomalononitrile tosylate, and the product, the substituted pyrazine 1-oxide, is allowed to react with phosphorus trichloride in tetrahydrofuran, according to the procedure of Taylor et al., J. Org. Chem. 38, 2817 (1973), to yield 2-amino-3-cyano-5-(4-bromophenyl)-6-methylpyrazine. This product is then hydrolyzed in sodium hydroxide and ethylene glycol and the 2-amino-3-carboxy-5-(4-bromophenyl)-6-methylpyrazine so obtained is decarboxylated by heating in tetrahydronaphthalene to yield 2-amino-5-(4-bromophenyl)-6-methylpyrazine.

Another intermediate, 2-amino-5,6-dimethylpyrazine is prepared from 2-chloro-5,6-dimethylpyrazine, which in turn is prepared according to the procedure of Karmas et al., J. Am. Chem. Soc. 74, 1580–1584 (1952).

Still other pyrazine intermediate compounds can be prepared starting with 2,5-dichloropyrazine, which itself can be prepared by the procedure of Palamidessi and Bernardi, J. Org. Chem. 29, 2491 (1964). This 2,5-dichloropyrazine can be used as the starting material for the phenoxy, phenylthio, or phenylsulfonyl substituted pyrazine intermediates, or the corresponding substituted phenoxy, phenylthio, or phenylsulfonyl substituted pyrazine intermediates. Thus, as a general procedure, 2,5-dichloropyrazine can be allowed to react with an equivalent of phenoxide or thiophenoxide ion in a suitable solvent such as ethanol, t-butanol, dimethylformamide, acetonitrile, or the like, at a temperature in the range of from about 0° to about 120° C., to yield the corresponding 2-chloro-5-phenoxy(or phenylthio)pyrazine. The 2-chloro-5-phenoxy(or phenylthio)-pyrazine can be converted to the corresponding 2-amino-5-phenoxy(or phenylthio)pyrazine by reaction with ammonium hydroxide at a temperature in the range of about 150°–200° C. in a high pressure reaction vessel for a time sufficient to give substantially complete conversion. The 2-amino-5-phenoxy(or phenylthio)pyrazine obtained in this manner can then be used to prepare the 1-(substituted benzoyl)-3-[5-phenoxy(or phenylthio)-2-pyrazinyl]ureas. Homologous phenoxy or phenylthio compounds can be prepared in the same general manner.

The 2-chloro-5-phenylthiopyrazine intermediate, or homolog thereof, can be oxidized to the 2-chloro-5-phenylsulfonylpyrazine intermediate through the use of such oxidizing agents as peracetic acid or m-chloroperbenzoic acid. Suitable solvents for use in carrying out this reaction include acetic acid, chloroform, methylene chloride, and the like. Suitable reaction temperatures for the oxidation can range from about 20° to about 70° C.

The 2-chloro-5-phenylsulfonylpyrazine can then be allowed to react with ammonia or ammonium hydroxide in a high pressure reaction vessel, at a temperature of about 100° to about 200° C. to yield the 2-amino-5-phenylsulfonylpyrazine intermediate. Reaction conditions may vary depending on the chemical structure of the phenylsulfonyl grouping.

The 2-aminoquinoxalines, which are simply aminobenzopyrazines, are also prepared by methods well known in the art. For example, 2-aminoquinoxaline is prepared by allowing the commercially available 2-chloroquinoxaline to react with ammonia in a suitable solvent such as ethanol at the temperature of a steam bath.

Other intermediate quinoxalines are prepared starting with the appropriate o-phenylenediamines, which may or may not be commercially available.

Some of the o-phenylenediamines which are not commercially available are readily prepared from the corresponding dinitroanilines by hydrogenation. The hydrogenations are carried out by using anhydrous hydrazine in the presence of 5% ruthenium on carbon (Engelhard Industries) in a suitable solvent, such as commercial absolute ethanol, at a temperature of about 55°–70° C. Thus, for example, 5-cyano-3-nitro-o-phenylenediamine is readily prepared by the selective hydrogenation of 4-cyano-2,6-dinitroaniline in the presence of 5% ruthenium on carbon in ethanol as solvent, together with anhydrous hydrazine. Following the same general procedure 3-nitro-5-trifluoromethyl-o-phenylenediamine is prepared from 2,6-dinitro-4-trifluoromethylaniline.

Other o-phenylenediamines useful in preparing the quinoxaline intermediates for synthesizing the novel compounds of this invention are prepared by reduction of commercially available o-nitroanilines through the use of 5% palladium on carbon catalyst in a low pressure hydrogenation apparatus. For example, 2-nitro-4-trifluoromethylaniline is reduced in this manner to yield 4-trifluoromethyl-o-phenylenediamine.

The 2-amino-6-chloroquinoxaline and 2-amino-7-chloroquinoxaline are prepared by methods well known in the art, and elegantly described in *The Chemistry of Heterocyclic Compounds, Condensed Pyridazine and Pyrazine Rings,* Part III, *Quinoxalines,* Chapter XXIV et seq., page 203 et seq., by J. C. E. Simpson, [Arnold Weissberger, Consulting Editor, Interscience Publishers, Inc., New York (1953)]. Thus, 3,4-diaminochlorobenzene is allowed to react with glyoxylic acid to yield a mixture of 6-chloro-2-hydroxyquinoxaline and 7-chloro-2-hydroxyquinoxaline. The mixture in turn is allowed to react with phosphorous oxychloride to yield a mixture of 2,6-dichloroquinoxaline and 2,7-dichloroquinoxaline. The mixture is allowed to react with anhydrous ammonia in a suitable solvent, dimethylsulfoxide being the solvent of choice, to yield a mixture of 2-amino-6-chloroquinoxaline and 2-amino-7-chloroquinoxaline.

The novel compounds of this invention are prepared by allowing the 2-aminopyrazine or 2-aminoquinoxaline intermediate compounds to react with a 2,6-disubstituted-benzoylisocyanate to yield the corresponding 1-(substituted benzoyl)-3-(substituted pyrazinyl)urea. The preparation is exemplified as follows: 2,6-dichlorobenzoylisocyanate is allowed to react with 2-amino-5-chloropyrazine in cold ethyl acetate. The reaction mixture is stirred overnight at room temperature. The product is isolated by evaporating the ethyl acetate solvent and adding a mixture of ether and hexane to the residue. A solid is precipitated which is then purified by recrystallization from a suitable solvent such as ethanol. There is obtained a product having a melting point of about 201°–204° C., which product is identified by elemental analyses and NMR and infrared spectra as 1-(5-chloro-2-pyrazinyl)-3-(2,6-dichlorobenzoyl)-urea.

Those novel compounds of the generic formula above wherein $R^7$ and $R^8$ form a ring system with the group

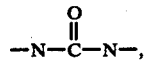

can be prepared following the procedures described by Wellinga et al., U.S. Pat. No. 3,748,356 (July 24, 1973). Thus, a 1-(substituted benzoyl)-3-(substituted pyrazinyl)urea is allowed to react under suitable conditions with, for example, a dihalodimethyl ether, or with oxalyl chloride, to yield a 3-(substituted pyrazinyl)-5-(substituted benzoyl)-2,3,5,6-tetrahydro-1,3,5-oxadiazin-4-one, or a 1-(substituted benzoyl)-3-(substituted pyrazinyl) parabanic acid, respectively.

The preparations of the intermediate substituted benzoylisocyanates, pyrazines, and benzopyrazines (quinoxalines) are illustrated by the following Preparations.

PREPARATION 1

2,6-Dichlorobenzoylisocyanate

This compound was prepared following the procedure of Speziale et al, J. Org. Chem. 27, 3742 (1962).

A solution of 47.5 g. of 2,6-dichlorobenzamide (commercially available) in 150 ml. of methylene dichloride was prepared. Twenty-eight ml. of oxalyl chloride was added very slowly to the solution. The mixture was refluxed overnight. The reaction product mixture was cooled and filtered and the filtrate evaporated to remove the solvent, methylene dichloride. The oily residue was distilled to yield product having a boiling point of about 69°–72° C. at 0.25 mm. The product, which weighed 20 g., was identified as 2,6-dichlorobenzoylisocyanate.

Following the same general procedure of Preparation 1, and starting with 2,6-dimethylbenzamide (prepared from commercially available 2,6-dimethylbenzoic acid), the following compound was synthesized:

2,6-Dimethylbenzoylisocyanate, as an oil.

Following the same general procedure of Preparation 1, and starting with 2,6-difluorobenzamide, the following compound was synthesized:

2,6-Difluorobenzoylisocyanate, as an oil.

PREPARATION 2

2-Amino-5-chloropyrazine

This compound was prepared stepwise. The first step followed the procedure of Dallacker et al., Ann. 660, 98–103 (1962).

Following that procedure, a mixture of 7.5 g. of 2-amino-3-carboxypyrazine, 8.9 g. of 1-methyl-3-p-tolyl-triazine, and 250 ml. of tetrahydrofuran was refluxed for about 4 hours. The reaction product mixture was cooled and filtered and the solid on the filter discarded. The filtrate was concentrated in vacuo to dryness and a small amount of ethyl ether was added to the residue. The solid which separated was collected. It weighed about 7 g. and had a melting point of about 166°–169° C. It was identified by infrared spectrum as methyl 2-amino-3-pyrazinylcarboxylate.

In the next step, a mixture of 2.8 g. of methyl 2-amino-3-pyrazinylcarboxylate, 100 ml. of water, and 23 ml. of glacial acetic acid was stirred at a temperature of about 40° C., and anhydrous chlorine bubbled through the mixture for about 25 minutes, while maintaining the temperature of the reaction mixture at about 35°–40° C. The reaction product mixture was cooled and filtered. The solid obtained was stirred for an hour in a mixture of 30 ml. of water and 4.6 g. of sodium sulfite, and filtered off. The solid which was collected was stirred in a mixture of ice and water and filtered off. The solid was identified by its NMR spectrum as methyl 2-amino-5-chloro-3-pyrazinylcarboxylate. The material was used as is without further purification.

Following the procedure of Palamidessi and Bernardi, J. Org. Chem. 29, 2491 (1964), the methyl 2-amino-5-chloro-3-pyrazinylcarboxylate was first hydrolyzed and then decarboxylated.

A mixture of 1.6 g. of methyl 2-amino-5-chloro-3-pyrazinylcarboxylate and 50 ml. of 2 N aqueous sodium hydroxide was refluxed for about 1.5 hours. The reaction product mixture was cooled and filtered. The solid which was collected was dissolved in 25 ml. of hot water, the solution filtered, and the filtrate acidified with concentrated aqueous hydrochloric acid. The solid which separated was filtered off and dried. It weighed 1.3 g., had a melting point of about 177° C. (dec.), and was identified by its infrared spectrum as 2-amino-3-carboxy-5-chloropyrazine. It was used as is without further purification.

A mixture of 500 mg. of 2-amino-3-carboxy-5-chloropyrazine and 9 ml. of tetrahydronaphthalene was refluxed for about 1 hour. The reaction product mixture was cooled and filtered. The solid which was collected was washed with hexane. The solid had a melting point of about 121°–123° C. (dec.), and was identified by NMR spectrum as 2-amino-5-chloropyrazine.

PREPARATION 3

2-Amino-5,6-dichloropyrazine

A mixture of 5 g. of 2-amino-6-chloropyrazine (commercially available), 10.3 g. of N-chlorosuccinimide, and 100 ml. of chloroform was refluxed for about 1.5 hours. The reaction mixture was cooled and filtered, the solid collected on the funnel being discarded. The filtrate was evaporated and the residue washed with water and hot aqueous sodium bisulfite solution, and the solid which formed under this treatment was collected on a funnel. The solid was chromatographed on a column of 5×8 mm. styrene and divinylbenzene copolymer beads using chloroform. There were obtained by this chromatography three compounds:

Compound 1, having a melting point of about 132°–135° C., was identified as 2-amino-3,6-dichloropyrazine.

Compound 2, having a melting point of about 132°–134° C., was identified as 2-amino-3,5,6-trichloropyrazine.

Compound 3, having a melting point of about 143°–144° C., was identified as 2-amino-5,6-dichloropyrazine, the desired compound.

PREPARATION 4

2-Aminoquinoxaline

Three g. of 2-chloroquinoxaline (commercially available) was dissolved in 50 ml. of dimethylsulfoxide and heated on the steam bath while anhydrous ammonia was bubbled into the mixture. The mixture was heated and stirred overnight on the steam bath. It was poured into 150 ml. of a mixture of ice and water, and the solid which precipitated was collected by filtration. This solid was recovered starting material and was discarded. The filtrate was cooled in an ice bath and the solid which precipitated was filtered off. This solid was identified by infrared spectrum as the desired compound, 2-aminoquinoxaline. It was used as is without further purification.

PREPARATION 5

Mixture of 2-amino-6-chloroquinoxaline and 2-amino-7-chloroquinoxaline

This intermediate was prepared stepwise.

A mixture of 25 g. of 3,4-diaminochlorobenzene, 17.5 g. of glyoxylic acid, and 150 ml. ethanol was refluxed for about 2 hours, and then stirred for about 48 hours at ambient room temperature. The reaction product mixture was concentrated in vacuo to remove the ethanol, leaving a solid residue. The solid residue was identified as a mixture of 6-chloro-2-hydroxyquinoxaline and 7-chloro-2-hydroxyquinoxaline, and was used in the next step of the preparation without further purification.

A mixture of 10 g. of the mixture of chlorohydroxyquinoxalines from above and 80 ml. of phosphorous oxychloride was refluxed for about 1 hour. The reaction product mixture was concentrated essentially to dryness in vacuo, and a mixture of tetrahydrofuran and water added to the residue. The solid which separated was filtered off and recrystallized from ethanol. The crystalline product thus obtained was identified by its NMR spectrum as being composed of two isomers, 2,6-dichloroquinoxaline and 2,7-dichloroquinoxaline. This mixture of isomers was used in the next step of the preparation without further purification.

A mixture of 3 g. of the mixture of 2,6-dichloroquinoxaline and 2,7-dichloroquinoxaline (prepared above) and 75 ml. of dimethylsulfoxide was prepared, and anhydrous ammonia bubbled through the mixture while heating the mixture overnight on the steam bath. The reaction product mixture was cooled to room temperature and poured into a mixture of ice and water with stirring, which stirring was continued for about one hour. At the end of that time, the aqueous mixture was filtered to recover the solid which had separated. The solid was examined by TLC and its infrared spectrum, and was identified as a mixture of 2-amino-6-chloroquinoxaline and 2-amino-7-chloroquinoxaline.

PREPARATION 6

2-Amino-5,6-dimethylpyrazine

This intermediate was prepared from 2-chloro-5,6-dimethylpyrazine, which chloro compound was prepared according to the procedure of Karmas et al., J. Am. Chem. Soc. 74, 1580–1584 (1952).

5.1 g. of 2-chloro-5,6-dimethylpyrazine was allowed to react with 200 ml. of concentrated ammonium hydroxide at 200° C. for about 10 hours in a stainless steel high pressure reaction vessel. The reaction vessel and contents were cooled. The reaction vessel was opened, and washed out with water. The aqueous solution of the reaction product mixture thus obtained was concentrated in vacuo to a volume of about 50–100 ml. This residual solution was saturated with sodium hydroxide pellets and extracted two times with 200 ml. portions of diethyl ether. The combined ether extracts were dried over anhydrous magnesium sulfate. The drying agent was filtered off and the filtrate concentrated in vacuo to dryness. The solid residue which was obtained was recrystallized from methanol to yield product having a melting point of about 144°–147° C. The product was identified by NMR and infrared spectra as 2-amino-5,6-dimethylpyrazine.

PREPARATION 7

2-Amino-5-methylpyrazine

This intermediate pyrazine was prepared via a stepwise procedure.

In the first step, a mixture of 5.0 g. of 2-oxopropanal 1-oxime [prepared by the method of Meyer et al., Chem. Ber. 11, 695 (1878)], and 14.5 g. of aminomalononitrile tosylate [prepared by the method of Ferris et al., J. Am. Chem. Soc. 88, 3829 (1966)], in 85 ml. of isopropyl alcohol was stirred overnight at room temperature. The reaction product mixture was filtered. The yellow solid which was collected weighed 6.4 g., and was identified by NMR and IR spectra as 2-amino-3-cyano-5-methylpyrazine 1-oxide. This product was used as is in the next step.

To the pyrazine 1-oxide (prepared above), 6.4 g., in 200 ml. of tetrahydrofuran, cooled to about 0° C., was added 35 ml. of phosphorus trichloride. The reaction mixture was stirred for about 2.5 hours while being allowed to warm to room temperature. At the end of that time, the reaction product mixture was concentrated in vacuo to a volume of about 10 ml. and poured into 500 ml. of ice and water. The solid which precipitated was filtered off and identified by NMR and IR spectra as 2-amono-3-cyano-5-methylpyrazine. Weight, 4 g.

In the next step, a mixture of 4 g. of 2-amino-3-cyano-5-methylpyrazine, 75 ml. of water, and 4 g. of sodium hydroxide was refluxed for about two hours. The reaction product mixture was cooled and filtered to collect the solid material. The solid was dissolved in a small amount of hot water, and the solution acidified to pH 5. The mixture was cooled and the solid filtered off. The solid was identified by IR spectrum as 2-amino-3-carboxy-5-methylpyrazine. It was used as is without further purification in the next step.

In the last step, a mixture of 2 g. of the carboxypyrazine (prepared above) and 10 ml. of tetrahydronaphthalene was refluxed for about two hours. The reaction product mixture was cooled and filtered. The solid which was collected was identified by its IR spectrum as 2-amino-5-methylpyrazine.

PREPARATION 8

2-Amino-5-phenyl-6-methylpyrazine

This intermediate pyrazine was prepared via a stepwise procedure.

In the first step, a mixture of 6.5 g. of 1-phenyl-1,2-propanedione-2-oxime (commercially available) and 10.1 g. of aminomalononitrile tosylate in 60 ml. of isopropyl alcohol was stirred overnight at room temperature. The reaction product mixture was filtered. The solid which was collected weighed 7 g. The solid was identified by NMR spectrum as 2-amino-3-cyano-5-phenyl-6-methylpyrazine 1-oxide.

A mixture of 7 g. of the pyrazine 1-oxide (prepared above) and 250 ml. of tetrahydrofuran was cooled to about 0° C., and 40 ml. of phosphorus trichloride was added slowly thereto. After addition was complete, the reaction mixture was stirred overnight at room temperature. The mixture was then concentrated in vacuo to a volume of about 50 ml., and the concentrate poured into one liter of a mixture of ice and water. The solid which precipitated was collected on a filter. The solid weighed 1 grams and was identified as 2-amino-3-cyano-5-phenyl-6-methylpyrazine.

In the next step, a mixture of 1 g. of the 2-amino-3-cyano-5-phenyl-6-methylpyrazine (prepared above), 50 ml. of ethylene glycol, and 500 mg. of sodium hydroxide was heated at about 150° C. for about 3 hours. The reaction product mixture was cooled, water was added, and the mixture neutralized to a pH of 5-7. The solid which precipitated was collected, and was identified by IR spectrum as 2-amino-3-carboxy-5-phenyl-6-methylpyrazine. This solid was used as is in the next step of the preparation.

The carboxypyrazine (prepared above), 500 mg., was refluxed in 5 ml. of tetrahydronaphthalene for about 2 hours. The reaction product mixture was cooled and hexane added thereto. The solid which precipitated was filtered off. It weighed 470 mg., and was identified by NMR and IR spectra as 2-amino-5-phenyl-6-methylpyrazine.

Following the same general procedure described in Preparation 8, and using as starting materials the indicated oximes, prepared as described by Hartung et al., J. Am. Chem. Soc. 51, 2262 (1929), additional pyrazine intermediates were prepared. These pyrazine intermediates were identified by NMR and IR spectra:

9. 2-Amino-5-(4-methoxyphenyl)-6-methylpyrazine, from 1-(4-methoxyphenyl)-1,2-propanedione-2-oxime.
10. 2-Amino-5-(4-chlorophenyl)-6-methylpyrazine, from 1-(4-chlorophenyl)-1,2-propanedione-2-oxime.
11. 2-Amino-5-(4-bromophenyl)-6-methylpyrazine, from 1-(4-bromophenyl)-1,2-propanedione-2-oxime.
12. 2-Amino-5-(4-n-butylphenyl)-6-methylpyrazine, from 1-(4-n-butylphenyl)-1,2-propanedione-2-oxime.
13. 2-Amino-5-($\alpha,\alpha,\alpha$-trifluoro-m-tolyl)-6-methylpyrazine, from 1-($\alpha,\alpha,\alpha$-trifluoro-m-tolyl)-1,2-propanedione-2-oxime.
14. 2-Amino-5-(4-biphenylyl)-6-methylpyrazine, from 1-(4-biphenylyl)-1,2-propanedione-2-oxime.
15. 2-Amino-5-(4-fluorophenyl)-6-methylpyrazine, from 1-(4-fluorophenyl)-1,2-propanedione-2-oxime.
16. 2-Amino-5-($\alpha,\alpha,\alpha$-trifluoro-p-tolyl)-6-methylpyrazine, from 1-($\alpha,\alpha,\alpha$-trifluoro-p-tolyl)-1,2-propanedione-2-oxime.
17. 2-Amino-5-(o-tolyl)-6-methylpyrazine, from 1-(o-tolyl)-1,2-propanedione-2-oxime.
18. 2-Amino-5-[(4-methylthio)phenyl]-6-methylpyrazine, from 1-(4-methylthiophenyl)-1,2-propanedione-2-oxime.
19. 2-Amino-5-(3-bromophenyl)-6-methylpyrazine, from 1-(3-bromophenyl)-1,2-propanedione-2-oxime.
20. 2-Amino-5-(2-chlorophenyl)-6-methylpyrazine, from 1-(2-chlorophenyl)-1,2-propanedione-2-oxime.
21. 2-Amino-5-cyclohexyl-6-methylpyrazine, from 1-cyclohexyl-1,2-propanedione-2-oxime.

Following the same general procedure described in Preparation 8, and using oximes prepared by the method of Claisen et al., Chem. Ber. 20, 2194 (1887), the following additional pyrazine intermediates were prepared, and identified by NMR and IR spectra:

22. 2-Amino-5-(2,4-xylyl)pyrazine, from 2,4-xylylglyoxal oxime.
23. 2-Amino-5-(3,4-dichlorophenyl)pyrazine, from 3,4-dichlorophenylglyoxal oxime.
24. 2-Amino-5-(3-trifluoromethylphenyl)pyrazine, from 3-trifluoromethylphenylglyoxal oxime.
25. 2-Amino-5-(p-tolyl)pyrazine, from p-tolylglyoxal oxime.
26. 2-Amino-5-(4-chlorophenyl)pyrazine, from 4-chlorophenylglyoxal oxime.
27. 2-Amino-5-(4-ethylphenyl)pyrazine, from 4-ethylphenylglyoxal oxime.
28. 2-Amino-5-(4-t-butylphenyl)pyrazine, from 4-t-butylphenylglyoxal oxime.
29. 2-Amino-5-(3-ethoxyphenyl)pyrazine, from 3-ethoxyphenylglyoxal oxime.
30. 2-Amino-5-(4-bromophenyl)pyrazine, from 4-bromophenylglyoxal oxime.

Following the same general procedure of Preparation 8, and using an oxime prepared according to the method of Meyer et al., Chem. Ber. 11, 695 (1878), the following additional pyrazine intermediate was prepared. It was identified by NMR and IR spectra:

31. 2-Amino-5-ethylpyrazine, from 2-oxobutanal oxime.

PREPARATION 32

2-Amino-5-(t-butyl)pyrazine

This intermediate pyrazine was synthesized starting with t-butylglyoxal, which was prepared according to the procedure of Fuson et al., J. Am. Chem. Soc. 61, 1938 (1939). The t-butylglyoxal oxime was then prepared as follows:

A mixture of 10.23 g. of t-butylglyoxal hemihydrate in 150 ml. of water was prepared and ammonium hydroxide added to adjust the pH to 4-5. To the mixture there was then added 6.3 g. of acetone oxime and the mixture stirred at room temperature for two days. The reaction product mixture was extracted three times with 100 ml. portions of ether. The ether extracts were combined and dried over anhydrous magnesium sulfate. The drying agent was filtered off and the filtrate evaporated to dryness. The residue obtained was recrystallized from petroleum ether (b.p. 60°-71° C.) to yield colorless needles having a melting point of about 48°–52° C. and weighing 1.9 g. The product was identified as t-butylglyoxal oxime.

Following the same general procedure of Preparation 8 above, this t-butylglyoxal oxime was allowed to react with aminomalononitrile tosylate in isopropyl alcohol to yield 2-amino-3-cyano-5-t-butylpyrazine 1-oxide.

The pyrazine 1-oxide obtained above was then allowed to react with phosphorus trichloride to yield 2-amino-3-cyano-5-t-butylpyrazine, which was in turn hydrolyzed and decarboxylated to yield 2-amino-5-(t-butyl)pyrazine, identified by IR spectrum.

PREPARATION 33

2-Amino-5-neopentylpyrazine

The starting oxime material for this pyrazine intermediate was prepared according to the procedure of Hartung et al., J. Am. Chem. Soc. 51, 2262 (1929), from methyl neopentyl ketone, and identified by IR and NMR spectra as neopentylglyoxal oxime.

Following the general procedure described in Preparation 7, neopentylglyoxal oxime was allowed to react with aminomalononitrile tosylate, and there was isolated 2-amino-3-cyano-5-neopentylpyrazine 1-oxide.

The 1-oxide was then transformed, as described in Preparation 7, into the desired 2-amino-5-neopentylpyrazine, identified by IR spectrum.

PREPARATION 34

2-Amino-5-(4-bromophenyl)-6-ethylpyrazine

This intermediate pyrazine was prepared stepwise.

Using 4-bromobutyrophenone as starting material, and following the procedure of Hartung et al., supra, there was prepared 1-(4-bromophenyl)-1,2-butanedione 2-oxime, identified by IR and NMR spectrum.

Following the general procedure of Preparation 7, the 1-(4-bromophenyl)-1,2-butanedione 2-oxime was used to prepare 2-amino-5-(4-bromophenyl)-6-ethylpyrazine, identified by IR and NMR spectrum.

PREPARATION 35

2-Amino-6-cyanopyrazine

This intermediate was prepared via a stepwise procedure.

A mixture of 21 g. of pyrazine-2-carboxamide, 85 ml. of glacial acetic acid, and 75 ml. of 30 percent hydrogen peroxide was heated at about 55° C. for about 35 hours. The reaction product mixture was cooled and filtered. The solid which was collected was extracted with n-butanol and the extracts discarded. The solid which was insoluble in n-butanol was recrystallized from hot water to yield a white solid having a melting point of about 302°–305° C. The solid was identified by elemental analyses as pyrazine-2-carboxamide 4-oxide.

To a mixture of 4 g. of the pyrazine oxide (prepared above) in 40 ml. of dimethylformamide cooled in an ice bath, there was quickly added 12 ml. of phosphorus oxychloride. The reaction mixture was poured into water and the aqueous mixture extracted with ethyl acetate, and the extracts saved. Additional water was added to the aqueous layer and the aqueous mixture extracted with hexane-ether. The ethyl acetate and hexane-ether extracts were combined and concentrated in vacuo to leave a residue. The residue was identified by elemental analyses and IR spectrum as 2-chloro-6-cyanopyrazine, and was used without further purification in the next step.

A mixture of 1 g. of the above chlorocyanopyrazine and 25 ml. of dimethyl sulfoxide was prepared and anhydrous ammonia was bubbled thereinto. The reaction mixture was stirred overnight and then poured into water. The aqueous mixture was extracted with ethyl acetate, and the extracts dried. The drying agent was filtered off and the solvent removed in vacuo to leave a solid which was identified by its IR spectrum as 2-amino-6-cyanopyrazine. It was used as is without further purification in the preparation of final products of the invention.

PREPARATION 36

3-Nitro-5-trifluoromethyl-o-phenylenediamine

One kilogram of 2,6-dinitro-4-trifluoromethylaniline (3.99 mole) (commercially available), and 25 g. of 5 percent ruthenium on carbon, in 12 liters of ethanol were stirred in a 22-l. five-neck round-bottom flask equipped with an overhead stirrer, two large-bore condensers, a thermometer, and an addition funnel. This mixture was heated to about 55°–60° C., and the heating bath drained. To the heated mixture was added in a rapid dropwise fashion 370 g. of 85 percent hydrazine hydrate (6.29 moles, 5% excess). The reaction temperature was allowed to rise to reflux. When the exotherm had ceased, the reaction was refluxed for about one hour. The hot solution was filtered through a pad of filter aid (Hyflo-Super Cel, a diatomaceous earth, Johns-Manville Products Corp.) which was then washed with hot ethanol. The combined filtrates were concentrated under vacuum and chilled. The solid which precipitated was filtered off, washed with cold ethanol and dried, to give 657 g. of crude product. The crude product was recrystallized from 2 liters of methanol by the addition of 2 liters of water and chilling to give 600 g. (68% yield) of red solid, having a melting point of about 125° C. The product was identified as 3-nitro-5-trifluoromethyl-o-phenylenediamine.

PREPARATION 37

2-Amino-6-trifluoromethylquinoxaline and 2-amino-7-trifluoromethylquinoxaline This intermediate compound was also prepared stepwise.

Twenty grams of 4-amino-3-nitrobenzotrifluoride (commercially available) dissolved in 200 ml. of ethanol was hydrogenated over 5% palladium on carbon.

A mixture of the material from the reduction process above, 9.7 g. of glyoxalic acid, and 250 ml. of ethanol was refluxed for about 2 hours with stirring. The reaction mixture was then stirred at room temperature over the weekend. The reaction product mixture was filtered and the solid obtained was recrystallized from ethanol, and filtered off. The filtrate was tagged as (A) and was saved. It was worked up as described later. Thin-layer chromatography of the solid in ether gave one spot. The solid had a melting point of about 254°–255° C., and was identified by NMR spectrum as 6-trifluoromethylquinoxalin-2-one.

A mixture of 3 g. of 6-trifluoromethylquinoxalin-2-one (prepared above) in 25 ml. of phosphorus oxychloride was refluxed for about 2 hours. The phosphorus oxychloride was removed in vacuo and water was added. The aqueous mixture was filtered and the solid which was obtained was recrystallized from ethanol. The product obtained had a melting point of about 117°–119° C. and weighed 1.6 g. It was identified by its NMR and IR spectra as 2-chloro-6-trifluoromethylquinoxaline and was used as is in the next step.

A mixture of 1.6 g. of 2-chloro-6-trifluoromethylquinoxaline (prepared above) and 35 ml. of dimethylsulfoxide was prepared and ammonia bubbled into the mixture. The mixture was heated on a steam bath for about 1 hour and then poured into a mixture of ice and water. The aqueous mixture was filtered. The solid which was collected had a melting point of about 169°–172° C., and weighed 1.2 g. The solid was identified by its IR spectrum as 2-amino-6-trifluoromethylquinoxaline.

The ethanol filtrate tagged (A), saved from the recrystallization of 6-trifluoromethylquinoxalin-2-one, above, was concentrated in vacuo to dryness and the residue obtained was recrystallized from benzene to yield a solid. A sample of this solid was examined by thin-layer chromatography in ether. The results indicated that this material obtained from filtrate (A) had a higher $R_f$ value than the previously isolated material (which had been identified as 6-trifluoromethylquinoxalin-2-one). This material from filtrate (A) was recrystallized again, this time from ethyl acetate, to yield a product having a melting point of about 204°–206° C., and identified as 7-trifluoromethylquinoxalin-2-one.

This 7-trifluoromethylquinoxalin-2-one was allowed to react with phosphorus oxychloride (in the same manner as described above for 6-trifluoromethylquinoxalin-2-one) to yield the intermediate 2-chloro-7-trifluoromethylquinoxaline having a melting point of about 119°–120° C. This compound was allowed to react with ammonia, in the manner described above, to yield the 2-amino-7-trifluoromethylquinoxaline, having a melting point of about 192°–194° C., and identified by IR spectrum.

PREPARATION 38

2-Amino-6-trifluoromethylpyrazine

This intermediate compound was prepared stepwise.

Aminoacetamidine dihydrobromide was prepared and identified according to the procedure of Mengelberg, Chem. Ber. 89, 1185 (1956). The preparation of 3,3-dibromo-1,1,1-trifluoropropanone was accomplished according to the procedure of McBee and Burton, J. Am. Chem. Soc. 74, 3902 (1952).

A mixture of 6.6 g. of 3,3-dibromo-1,1,1-trifluoropropanone, 60 ml. of water, and 6.6 g. sodium acetate was refluxed for about 10 minutes. The solution thus obtained was cooled and added dropwise to a solution of 6 g. of aminoacetamidine dihydrobromide in 90 ml. of methanol cooled to a temperature of about −30° C., followed by the addition of a solution of 3.6 g. of sodium hydroxide pellets in 25 ml. of water. The reaction mixture was stirred and warmed gradually to about 20° C. over a period of about two hours. The reaction product mixture was concentrated in vacuo to remove the methanol, and the residue extracted with ethyl acetate. There was obtained product weighing 3.6 g. and having a melting point of about 133°–136° C. after recrystallization from a mixture of benzene and hexane. The product was identified by NMR spectrum and elemental analyses as 2-amino-6-trifluoromethylpyrazine.

| Analyses calcd. for $C_5H_4F_3N_3$: | | |
|---|---|---|
| | Theoretical | Found |
| C | 36.82% | 37.11% |
| H | 2.47 | 2.17 |
| N | 25.76 | 25.52 |

PREPARATION 39

2-Amino-5-trifluoromethylpyrazine

A solution of 18 g. of 4,5-diamino-6-hydroxypyrimidine sulfate (commercially available) in 180 ml. of aqueous 3 N sodium hydroxide was prepared, and to the cooled reaction there was added 25.2 g. of 3,3-dibromo-1,1,1-trifluoropropanone. The reaction mixture was stirred for about 48 hours at room temperature. The precipitate which formed was filtered off, dissolved in 140 ml. of aqueous 60% sulfuric acid, and heated at about 135° C. for about 8 hours. The reaction mixture was poured over crushed ice and the aqueous mixture neutralized using concentrated aqueous ammonium hydroxide. The solution was then extracted with ethyl acetate. The ethyl acetate extracts were concentrated in vacuo to dryness and the residue recrystallized from a mixture of benzene and hexane to yield product weighing 2.2 g., and having a melting point of about 118°–122° C. The product was identified by NMR spectrum and elemental analyses as 2-amino-5-trifluoromethylpyrazine.

| Analyses calcd. for $C_5H_4F_3N_3$: | | |
|---|---|---|
| | Theoretical | Found |
| C | 36.82% | 37.04% |
| H | 2.47 | 2.58 |
| N | 25.76 | 25.97 |

PREPARATION 40

2-Amino-5-phenyl-6-trifluoromethylpyrazine

This intermediate was prepared stepwise.

Following the procedure of Lombardino, J. Het. Chem., 10, 697 (1973), there was prepared 1-phenyl-3,3,3-trifluoro-1,2-propanedione monohydrate.

To a solution of 1.8 g. of 1-phenyl-3,3,3-trifluoro-1,2-propanedione monohydrate in 40 ml. of methanol, cooled in an ice bath, there was added, with stirring, 2 g. of aminoacetamidine dihydrobromide. Stirring was continued while 8.6 ml. of aqueous 2 N sodium hydroxide was added. The reaction mixture was then stirred at room temperature for about two hours, and then stirred and refluxed for about four hours. The reaction mixture was cooled and acidified with dilute aqueous hydrochloric acid. Water was added, and the mixture extracted with 100 ml. of ethyl acetate. The ethyl acetate extract was dried over anhydrous magnesium sulfate, the drying agent filtered off, and the filtrate concentrated in vacuo. The residue thus obtained was dissolved in chloroform, and chromatographed on a silica gel column using chloroform as the eluant. There was obtained material weighing 100 mg., and identified as 2-amino-5-phenyl-6-trifluoromethylpyrazine.

PREPARATION 41

2-Amino-5-(4-bromophenyl)-6-chloropyrazine

This compound was prepared stepwise.

Step 1. A mixture of 37 g. of 1-(4-bromophenyl)-1,2-propanedione-2-oxime, 34 g. of the tosylate salt of ethyl aminocyanoacetate, and 750 ml. isopropanol was stirred at room temperature for about 6 days. Another 12 g. of the above-identified tosylate salt was added to the reaction mixture and stirring at room temperature continued for 24 hours. Another 3 g. of the tosylate salt was added to the reaction mixture and stirring continued at room temperature for several more days. The reaction mixture was cooled, and the solid which precipitated was filtered off. The solid was extracted with 2 liters of boiling ethyl acetate, and the solid filtered off. The filtrate was concentrated in vacuo to about 90 ml. The solution was filtered again and then cooled. The crystalline material which separated was filtered off. It had a melting point of about 200°–205° C., and was identified by NMR spectrum as 2-amino-5-(4-bromophenyl)-3-carbethoxypyrazine-1-oxide. Yield: 11 g.

Step 2. A mixture of 60 ml. of phosphorus oxychloride, 10 ml. dimethylformamide was stirred and 12.1 g. of 2-amino-5-(4-bromophenyl)-3-carboethoxypyrazine-1-oxide (prepared as above) added in small amounts. When the addition was complete, the reaction mixture was stirred at reflux for about 15 minutes, after which the excess phosphorus oxychloride was removed in vacuo. Ice was added very carefully to the residue, and the mixture made basic by adding solid sodium bicarbonate. The mixture was extracted with 800 ml. of chloroform and the chloroform extract dried over anhydrous magnesium sulfate. The drying agent was filtered off and the filtrate concentrated to dryness in vacuo to leave a black solid. The black solid was extracted with 4×500 ml. portions of boiling cyclohexane. The combined cyclohexane extracts were combined and concentrated to a volume of about 300 ml. A beige solid separated which had a melting point of about 151°–153° C., and which was identified by NMR spectrum as 5-(4-bromophenyl)-3-carbethoxy-6-chloro-2-{[(dimethylamino)methylene]imino}pyrazine. Yield: 10.5 g.

Step 3. A mixture of 12 g. of 5-(4-bromophenyl)-3-carbethoxy-6-chloro-2-{[(dimethylamino)methylene]imino}-pyrazine (prepared as in Step 2, above) and 150 ml. of aqueous 2 N hydrochloric acid was stirred and refluxed for about 5 minutes, during which time a white precipitate formed. The mixture was cooled and about 50 ml. of aqueous 1 N sodium hydroxide solution was added. The mixture was filtered and the solid which was collected on the filter was washed with water. A sample of the solid recrystallized from ethanol had a melting point of about 207°–208° C., and was identified by NMR spectrum and elemental analyses as 2-amino-5-(4-bromophenyl)-3-carbethoxy-6-chloropyrazine. Yield: 10 g.

| Analyses calculated for $C_{13}H_{11}BrClN_3O_2$: | | |
| --- | --- | --- |
| | Theoretical | Found |
| C | 43.79 | 43.90 |
| H | 3.11 | 3.33 |
| N | 11.78 | 11.59 |

Step 4. A mixture of 10 g. of the 2-amino-5-(4-bromophenyl)-3-carbethoxy-6-chloropyrazine, 75 ml. of dioxane, 75 ml. of water, and 8 g. of sodium hydroxide pellets was heated briefly to refluxing, at which time complete solution was obtained. The mixture was acidified with acetic acid and cooled. The solid which separated was filtered off and slurried with aqueous 1 N hydrochloric acid. The mixture was filtered to collect the solid product. A sample recrystallized from ethanol had melting point of about 212°–214° C., and was identified by NMR spectrum and elemental analyses at 2-amino-5-(4-bromophenyl)-3-carboxy-6-chloropyrazine. Yield: 9 g.

| Analyses calculated for $C_{11}H_7BrClN_3O_2$: | | |
| --- | --- | --- |
| | Theoretical | Found |
| C | 40.21 | 40.10 |
| H | 2.15 | 2.23 |
| N | 12.79 | 12.63 |

Step 5. A mixture of 9 g. of 2-amino-5-(4-bromophenyl)-3-carboxy-6-chloropyrazine and 50 ml. of tetralin was refluxed for about 15 minutes. The mixture was cooled and 75 ml. of hexane was added. The solid which separated was filtered off and washed with hexane. The solid was recrystallized from ethyl acetate to yield product having a melting point of about 254°–256° C. and identified by NMR spectrum as 2-amino-5-(4-bromophenyl)-6-chloropyrazine. Yield: 4 g.

The synthesis of the novel compounds of this invention are exemplified by the following examples, but the scope of the invention is not to be considered as limited thereby.

EXAMPLE 1

3-(5-Chloro-2-pyrazinyl)-1-(2,6-dichlorobenzoyl)urea

To a mixture of 250 mg. of 2-amino-5-chloropyrazine in 50 ml. of cold ethyl acetate was added 450 mg. of 2,6-dichlorobenzoylisocyanate and the mixture stirred overnight. The reaction product mixture was concentrated in vacuo to remove the ethyl acetate, and a mixture of ether and hexane added. The solid which precipitated was filtered off. The solid was recrystallized from ethanol to yield product having a melting point of about 201°–204° C. The product was identified by elemental analyses and NMR and infrared spectra as 3-(5-chloro-2-pyrazinyl)-1-(2,6-dichlorobenzoyl)urea.

Following the same general procedure of Example 1, and using appropriate starting materials, the following additional compounds were prepared and identified by elemental analyses, NMR and infrared spectra.

1A. 1-(2,6-Dichlorobenzoyl)-3-(5-phenyl)-2-pyrazinyl)urea, having a melting point of about 216°–219° C.

1B. 1-(2,6-Dichlorobenzoyl)-3-(5,6-dichloro-2-pyrazinyl)urea, having a melting point of about 210°–213° C.

1C. 1-(6-Chloro-2-pyrazinyl)-3-(2,6-dichlorobenzoyl)urea, having a melting point of about 234°–235° C.

1D. 1-(2,6-Dichlorobenzoyl)-3-(2-quinoxalinyl)-urea, having a melting point of about 230°–233° C.

1E. A mixture of 1-(6-chloro-2-quinoxalinyl)-3-(2,6-dichlorobenzoyl)urea and 1-(7-chloro-2-quinoxalinyl)-3-(2,6-dichlorobenzoyl)urea, the mixture having a melting point of about 154°–161° C.

1F. 1-(2,6-Dichlorobenzoyl)-3-(5,6-dimethyl-2-pyrazinyl)urea, having a melting point of about 214°–215° C.

1G. 3-(5-Bromo-2-pyrazinyl)-1-(2,6-dichlorobenzoyl)-urea, having a melting point of about 208°–210° C.

1H. 1-(2,6-Dimethylbenzoyl)-3-(5-phenyl-2-pyrazinyl)urea, having a melting point of about 201°–204° C.

1J. 1-(2,6-Dichlorobenzoyl)-3-(6-methyl-5-phenyl-2-pyrazinyl)urea, having a melting point of about 211°–212° C.

1K. 1-(6-Cyano-2-pyrazinyl)-3-(2,6-dichlorobenzoyl)urea, having a melting point of about 192°–197° C.

1L. 1-(2,6-Dichlorobenzoyl)-3-(5-methyl-2-pyrazinyl)urea, having a melting point of about 233°–234° C.

1M. 1-(2,6-Dichlorobenzoyl)-3-[5-(4-chlorophenyl)-2-pyrazinyl]urea, having a melting point of about 245°–248° C.

1N. 1-(2,6-Dichlorobenzoyl)-3-[5-(p-tolyl)-2-pyrazinyl]urea, having a melting point of about 227°–229° C.

1O. 1-(2,6-Dichlorobenzoyl)-3-[5-(3-trifluoromethylphenyl)-2-pyrazinyl]urea, having a melting point of about 188°–193° C.

1P. 1-(2,6-Dichlorobenzoyl)-3-(5-ethyl-2-pyrazinyl)urea, having a melting point of about 211°–213° C.

1Q. 1-(2,6-Dichlorobenzoyl)-3-[6-methyl-5-(4-bromophenyl)-2-pyrazinyl]urea, having a melting point of about 225°–227° C.

1R. 1-(2,6-Dichlorobenzoyl)-3-(5-neopentyl-2-pyrazinyl)urea, having a melting point of about 218°–221° C.

1S. 1-(2,6-Dichlorobenzoyl)-3-(5-t-butyl-2-pyrazinyl)urea, having a melting point of about 207°–209° C.

1T. 1-(2,6-Dichlorobenzoyl)-3-[5-(3,4-dichlorophenyl)-2-pyrazinyl]urea, having a melting point of about 222°–223° C.

1U. 1-(2,6-Dichlorobenzoyl)-3-[6-methyl-5-(4-chlorophenyl)-2-pyrazinyl]urea, having a melting point of about 221°–223° C.

1V. 1-(2,6-Dichlorobenzoyl)-3-[5-(2,4-xylyl)-2-pyrazinyl]urea, having a melting point of about 221°–223° C.

1W. 1-(2,6-Dichlorobenzoyl)-3-[6-methyl-5-(4-anisyl)-2-pyrazinyl]urea, having a melting point of about 203°–206° C.

1X. 1-(2,6-Dichlorobenzoyl)-3-(8-nitro-6-trifluoromethyl-2-quinoxalinyl)urea, having a melting point of about 223° C.

1Y. 1-(2,6-Dichlorobenzoyl)-3-(6-trifluoromethyl-2-quinoxalinyl)urea, having a melting point of about 233° C. (dec.).

1Z. 1-(2,6-Dichlorobenzoyl)-3-(7-trifluoromethyl-2-quinoxalinyl)urea, having a melting point of about 222°–225° C.

1AA. 1-[5-(4-Bromophenyl)-6-ethyl-2-pyrazinyl]-3-(2,6-dichlorobenzoyl)urea, having a melting point of about 213°–215° C.

1AB. 1-(2,6-Dichlorobenzoyl)-3-[5-(2-naphthyl)-2-pyrazinyl]urea, having a melting point of about 220°–222° C.

1AC. 1-(2,6-Dichlorobenzoyl)-3-[5-(4-ethylphenyl)-2-pyrazinyl]urea, having a melting point of about 228°–229° C.

1AD. 1-(2,6-Dichlorobenzoyl)-3-[6-(trifluoromethyl)-2-pyrazinyl]urea, having a melting point of about 188°–192° C.

1AE. 1-[5-(4-t-Butylphenyl)-2-pyrazinyl]-3-(2,6-dichlorobenzoyl)urea, having a melting point of about 245°–246° C.

1AF. 1-[5-(4-Butylphenyl)-6-methyl-2-pyrazinyl]-3-(2,6-dichlorobenzoyl)urea, having a melting point of about 206°–208° C.

1AG. 1-(2,6-Dichlorobenzoyl)-3-[5-(trifluoromethyl)-2-pyrazinyl]urea, having a melting point of about 185°–188° C.

1AH. 1-(2,6-Dichlorobenzoyl)-3-[6-methyl-5-($\alpha,\alpha,\alpha$-trifluoro-m-tolyl)-2-pyrazinyl]urea, having a melting point of about 182°–185° C.

1AI. 1-[5-(4-Bromophenyl)-6-methyl-2-pyrazinyl]-3-(2,6-difluorobenzoyl)urea, having a melting point of about 241°–242° C.

1AJ. 1-[5-(4-Biphenylyl)-6-methyl-2-pyrazinyl]-3-(2,6-dichlorobenzoyl)urea, having a melting point of about 219°–221° C.

1AK. 1-(2,6-Dichlorobenzoyl)-3-[5-(4-fluorophenyl)-6-methyl-2-pyrazinyl]urea, having a melting point of about 209°–212° C.

1AL. 1-(2,6-Dichlorobenzoyl)-3-[6-methyl-5-($\alpha,\alpha,\alpha$-trifluoro-p-tolyl)-2-pyrazinyl]urea, having a melting point of about 214°–217° C.

1AM. 1-(2,6-Dichlorobenzoyl)-3-[5-phenyl-6-(trifluoromethyl)-2-pyrazinyl]urea, having a melting point of about 192°–194° C.

1AN. 1-(2,6-Dichlorobenzoyl)-3-[6-methyl-5-(o-tolyl)-2-pyrazinyl]urea, having a melting point of about 201°–208° C.

1AO. 1-(2,6-Dichlorobenzoyl)-3-[6-methyl-5-(4-methylthio)phenyl-2-pyrazinyl]urea, having a melting point of about 208°–212° C.

1AP. 1-[5-(3-Bromophenyl)-6-methyl-2-pyrazinyl]-3-(2,6-dichlorobenzoyl)urea, having a melting point of about 175°–178° C.

1AQ. 1-[5-(2-Chlorophenyl)-2-pyrazinyl]-3-(2,6-dichlorobenzoyl)urea, having a melting point of about 193°–197° C.

1AR. 1-[5-Cyclohexyl-6-methyl-2-pyrazinyl]-3-(2,6-dichlorobenzoyl)urea, having a melting point of about 231°–234° C.

1AS. 1-[5-(3-Ethoxyphenyl)-2-pyrazinyl]-3-(2,6-dichlorobenzoyl)urea, having a melting point of about 196°–200° C.

1AT. 1-[5-(4-Bromophenyl)-pyrazinyl]-3-(2,6-dichlorobenzoyl)urea, having a melting point of about 244°–254° C.

1AU. 1-[5-(4-Bromophenyl)-6-methyl-2-pyrazinyl]-3-(2,6-dimethylbenzoyl)urea, having a melting point of about 223°–225° C.

1AV. 1-[5-(4-bromophenyl)-6-chloro-2-pyrazinyl]-3-(2,6-dichlorobenzoyl)urea, having a melting point of about 229°–231° C.

The compounds of the present invention are useful for the control of insects of various orders, including Coleoptera such as Mexican bean beetle, boll weevil, corn rootworm, cereal leaf beetle, flea beetles, borers, Colorado potato beetle, grain beetles, alfalfa weevil, carpet beetle, confused flour beetle, powder pust beetle, wireworms, rice weevil, rose beetle, plum curculio, white grubs; Diptera, such as house fly, yellow fever mosquito, stable fly, horn fly, blowfly, cabbage maggot, carrot rust fly; Lepidoptera, such as Southern armyworm, codling moth, cutworm, clothes moth, Indianmeal moth, leaf rollers, corn earworm, European corn borer, cabbage worm, cabbage looper, cotton bollworm, bagworm, eastern tent caterpillar, sod webworm, fall armyworm; and Orthoptera, such as German cockroach and American cockroach.

It has been found that the novel compounds of the invention interfere with the mechanism of metamorphosis which occurs in insects, causing the death of the insects.

The novel compounds of this invention are formulated for use as insecticides by being mixed with a solid carrier material or dissolved or dispersed in a liquid carrier material. Included in such mixtures, if desired, are adjuvants such as surface-active substances and stabilizers.

These formulations can include aqueous solutions and dispersions, oil solutions and oil dispersions, pastes, dusts, wettable powders, miscible oils, granules, aerosol preparations and the like.

The wettable powders, pastes and miscible oils are formulations in concentrated form which are diluted with water before or during use.

The granular preparations are produced by taking up the novel compound in a solvent, after which granular carrier material such as porous granules, for example, pumice or attapulgite clay, mineral non-porous granules, such as sand or ground marl, and organic granules are impregnated with the solution, suitably in the presence of a binder. Such preparations contain about 1 to about 15 percent active ingredient, suitably about 5 percent.

Dust formulations are prepared by intimately mixing the active compound with an inert solid carrier material in a concentration of for example from about 1 to about 50 percent by weight. Examples of suitable solid carrier materials include talc, kaolin, diatomaceous earth, dolomite, gypsum, chalk, bentonite, attapulgite or mixtures of these and similar substances. It is also possible to use organic carrier materials such as ground walnut shells or the like.

Wettable powder formulations are produced by mixing from about 10 to about 80 parts by weight of a solid inert carrier, such as one of the aforementioned carrier materials, with from about 10 to about 80 parts by weight of the active compound, together with from about 1 to about 5 parts by weight of a dispersing agent, such as for example, the ligninsulfonates or alkylnaphthalenesulfonates, and preferably also with from about 0.5 to about 5 parts by weight of a wetting agent, such as one of the fatty alcohol sulfates, alkylarylsulfonates, or fatty acid condensation products.

Miscible oil formulations are prepared by dissolving the active compound in or suspending the active compound in a suitable solvent which is preferably rather immiscible with water, after which an emulsifier is added to the preparation. Suitable solvents include xylene, toluene, high aromatic petroleum distillates, for example solvent naphtha, distilled tar oil, and mixtures of these. Suitable emulsifiers include alkylphenoxypolyglycol ethers, polyoxyethylene sorbitan esters of fatty acids, or polyoxyethylene sorbitol esters of fatty acids. These miscible oils contain the active compound in a concentration of about 2 percent to about 50 percent by weight.

Where an aerosol preparation is desired, such aerosol preparation can be obtained in the usual manner by incorporating the active compound in a solvent in a volatile liquid suitable for use as a propellant, for example, one of the commercially available fluorocarbon propellants.

As is well understood, the preparations containing one of the active compounds of this invention may also include other known pesticidal compounds. This of course broadens the spectrum of activity of the preparation.

The amount of 1-(substituted benzoyl)-3-(substituted pyrazinyl)urea to be applied for insect control purposes to a given area of plant life is, of course, dependent upon a variety of factors, such as the extent of vegetative surface to be covered, the severity of the insect infestation, the condition of the foliage treated, the temperature, the humidity, etc. In general, however, the application of sufficient formulation to result in an application rate of the active ingredient of about 0.1 to about 1000 ppm. is desirable.

The insecticidal activity of the novel compounds of this invention has been determined by testing the efficacy of formulations of the compounds against Mexican bean beetle larvae (*Epilachna varivestia*), and against Southern armyworm larvae (*Spodoptera eridania*) in an insecticide screen. These insects are members of the Coleoptera and Lepidoptera orders of insects, respectively. The compounds have been tested in several tests against these insects at rates of from about 1000 ppm. down to about 1 ppm, the compounds being applied at these rates to leaves of plants upon which the above-identified larvae feed.

Experiment 1

The following procedure was used to evaluate the efficacy of the novel compounds of this invention as insecticides.

Bean plants were grown in four-inch square pots, with there being 6 to 10 plants per pot. When the plants were 10 days old, they were ready for use in this experiment.

Each test compound was formulated by dissolving 10 mg. of the test compound in 1 ml. of solvent (23 g. Toximul R plus 13 g. Toximul S per liter of 1:1 anhydrous ethanol and acetone) followed by mixing with 9 ml. of water to give a 1000 parts per million concentration of the test compound in the solution. (Toximul R and Toximul S are each a sulfonate/nonionic blend produced by Stepan Chemical Company, Northfield, Illinois.) This solution of test compound was then sprayed onto the 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae (*Epilachna varivestis*) and five second- and third-instar Southern armyworm larvae (*Spodoptera eridania*) were placed in each of three dishes. The dishes were then placed in a room wherein the temperature and relative humidity were controlled at about 78° C. and about 51 percent, respectively, for a period of about four days, at which time the first evaluation of the effects of the test compounds was made. After this evaluation, two fresh leaves from the original treated pots were placed in each dish. The dishes were again maintained in the temperature and humidity controlled room for an additional three days until the final seven day evaluation was made.

The percent control was determined by counting the number of living larvae per dish. All the treatments were compared to solvent controls and nontreated controls. The rating code (percent of control) used was as follows:
 0=0%
 1=1–50%
 2=51–99%
 3=100% control The results of this test are set forth in Table 1, which follows. In the table, column 1 identifies the compounds by the number of the preparative example; and columns 2 through 5 giving the Rating Code at days 4 and 7 for the two insects against which the compounds were tested at the application rate of 1000 ppm.

Table 1

| Compound | Rating Code | | | |
|---|---|---|---|---|
| | Mexican Bean Beetle | | Southern Armyworm | |
| | Day 4 | Day 7 | Day 4 | Day 7 |
| 1 | 0 | 1 | 3 | 3 |
| 1A | 0 | 0 | 3 | 3 |
| 1B | 0 | 1.5 | 0 | 1 |
| 1C | 0 | 0 | 3 | 3 |
| 1D | 0 | 0 | 2 | 2.5 |
| 1E | 0 | 0 | 2 | 3 |
| 1F | 0 | 0 | 0 | 2 |
| 1G | 0 | 3 | 3 | 3 |
| 1H | 0 | 0 | 1 | 2 |
| 1J | 0 | 2 | 0 | 3 |
| 1K | 0 | 0 | 2 | 3 |
| 1L | 2 | 2 | 2 | 2 |
| 1M | — | 0 | — | 3 |
| 1N | — | 0 | — | 3 |
| 1O | — | 1 | — | 3 |
| 1P | 0 | 1 | 2 | 2 |
| 1Q | 1 | 1 | 3 | 3 |
| 1R | 0 | 1 | 2 | 3 |
| 1S | 0 | 1 | 2 | 3 |
| 1T | 0 | 0 | 1 | 3 |
| 1U | 1 | 2 | 3 | 3 |
| 1V | 0 | 0 | 3 | 3 |
| 1W | 0 | 1 | 3 | 3 |
| 1Y | 1 | 1 | 3 | 3 |
| 1Z | 3 | 3 | 0 | 0 |
| 1AA | 0 | 1 | 3 | 3 |
| 1AC | 1 | 2 | 3 | 3 |
| 1AD | 1 | 2 | 3 | 3 |
| 1AE | 0 | 0 | 1 | 2 |
| 1AF | 2 | 3 | 2 | 3 |
| 1AG | 2 | 3 | 3 | 3 |
| 1AH | 2 | 2 | 2 | 3 |
| 1AI | 2 | 3 | 3 | 3 |
| 1AJ | 2 | 2 | 1 | 3 |
| 1AK | — | — | 3 | 3 |
| 1AL | 0 | 2 | 3 | 3 |
| 1AM | 0 | 2 | 3 | 3 |
| 1AN | 0 | 1 | 3 | 3 |
| 1AO | 0 | 2 | 3 | 3 |
| 1AP | 0 | 2 | 3 | 3 |
| 1AQ | 0 | 0 | 3 | 3 |
| 1AR | 0 | 2 | 1 | 2 |
| 1AS | 0 | 1 | 3 | 3 |
| 1AT | 0 | 1 | 3 | 3 |
| 1AU | 1 | 2 | 3 | 3 |
| 1AU | 1 | 2 | 3 | 3 |

EXPERIMENT 2

Several of the novel compounds tested in Experiment 1, above, were retested, this time at lower levels of application. The preparation of the bean plants was the same. The test compounds were formulated in the manner described hereinbelow:

Ten mg. of test compound was dissolved in 1 ml. of solvent and mixed with 9 ml. of water to give a 1000 ppm solution.

This solution was then serially diluted to obtain the necessary concentrations of solution for conducting the tests.

The solvent used was 50:50 alcohol:acetone plus 23 g. of Toximul R and 13 g. of Toximul S per liter.

The percent control was determined by counting the number of living larvae per dish and using Abbott's formula [W. W Abbott, "A Method of Computing the Effectiveness of an Insecticide", J. Econ. Entomol. 18, 265–7 (1925)]:

$$\text{Percent Control} = \frac{\text{No. of survivors in control} - \text{No. of survivors in treatment} \times 100}{\text{No. survivors in control}}$$

The results are set forth in Table 2, which follows. Where more than one replicate was run the recorded results are averages.

Table 2

| Compound | Appln. Rate ppm. | Percent Control Southern Armyworm | |
|---|---|---|---|
| | | Day 4 | Day 7 |
| 1 | 100 | 100 | 100 |
| | 50 | 100 | 100 |
| | 25 | 76 | 100 |
| | 12.5 | 50 | 96 |
| 1A | 1000 | 100 | 100 |
| | 100 | 92 | 100 |
| | 10 | 30 | 84 |
| 1C | 100 | 86 | 100 |
| | 50 | 74.5 | 96.5 |
| | 25 | 26.5 | 58.5 |
| | 12.5 | 7 | 27 |
| 1G | 100 | —* | 100 |
| | 25 | — | 100 |
| | 10 | — | 46 |
| | 5 | — | 46 |
| 1J | 100 | — | 100 |
| | 50 | — | 100 |
| | 25 | — | 100 |
| | 10 | — | 100 |
| | 5 | — | 74 |
| 1M | 100 | — | 100 |
| | 50 | — | 100 |
| | 25 | — | 100 |
| | 10 | — | 84 |
| | 5 | — | 28 |
| 1N | 100 | — | 100 |
| | 50 | — | 100 |
| | 25 | — | 100 |
| | 10 | — | 36 |
| 1O | 100 | — | 100 |
| | 50 | — | 100 |
| | 25 | — | 92 |
| 1Q | 100 | — | 100 |
| | 50 | — | 100 |
| | 25 | 100 | 100 |
| | 20 | 100 | 100 |
| | 10 | 100 | 100 |
| | 5 | 67 | 100 |
| | 2.5 | — | 93 |
| | 1 | 20 | 23 |
| 1R | 100 | 0 | 99 |
| 1U | 100 | — | 100 |
| | 50 | — | 100 |
| | 25 | — | 100 |
| | 10 | — | 100 |
| | 5 | — | 91.7 |
| | 2.5 | — | 71 |
| | 1 | — | 3 |
| 1V | 100 | 100 | 100 |
| | 50 | 100 | 100 |
| | 25 | 100 | 100 |
| | 10 | 32 | 73 |
| | 5 | 3 | 4 |
| | 1 | 0 | 0 |
| 1W | 100 | — | 100 |
| | 50 | — | 100 |
| | 25 | — | 100 |
| | 10 | — | 33 |
| | 5 | — | 0 |
| | 1 | — | 0 |
| 1AA | 50 | 60 | 100 |
| | 25 | 0 | 38 |
| | 10 | 0 | 38 |
| 1AB | 100 | — | 75 |
| 1AC | 100 | 100 | 100 |
| | 50 | 100 | 100 |
| | 25 | 100 | 100 |

Table 2-continued

| Compound | Appln. Rate ppm. | Percent Control Southern Armyworm | |
|---|---|---|---|
| | | Day 4 | Day 7 |
| | 10 | 0 | 17 |
| 1AD | 100 | 80 | 100 |
| | 50 | 30 | 96 |
| | 25 | 16 | 93 |
| | 10 | 3 | 36 |
| | 5 | 0 | 3 |
| 1AG | 100 | 100 | 100 |
| | 50 | 93 | 100 |
| | 25 | 86 | 100 |
| | 10 | 83 | 100 |
| | 5 | 73 | 96 |
| | 2.5 | 10 | 73 |
| 1AH | 100 | 100 | 100 |
| | 50 | 100 | 100 |
| | 25 | 100 | 100 |
| | 10 | 100 | 100 |
| | 5 | 35 | 100 |
| | 2.5 | 0 | 94 |
| | 1.0 | 0 | 12 |
| 1AI | 100 | 100 | 100 |
| | 50 | 100 | 100 |
| | 25 | 93 | 100 |
| | 10 | 90 | 96 |
| | 5 | 93 | 100 |
| | 2.5 | 87 | 100 |
| | 1.0 | 18 | 71 |
| 1AJ | 50 | 53 | 100 |
| | 25 | 46 | 100 |
| | 10 | 0 | 46 |
| | 5 | 0 | 0 |
| 1AK | 100 | 100 | 100 |
| | 50 | 92 | 100 |
| | 25 | 92 | 100 |
| | 10 | 92 | 100 |
| | 5 | 57 | 100 |
| | 2.5 | 12 | 81 |
| 1AL | 50 | 100 | 100 |
| | 25 | 100 | 100 |
| | 10 | 100 | 100 |
| | 5 | 60 | 100 |
| | 2.5 | 89 | 100 |
| | 1.0 | 0 | 67 |
| 1AM | 100 | 60 | 86 |
| | 50 | 53 | 93 |
| | 25 | 10 | 43 |
| 1AN | 100 | 80 | 100 |
| | 50 | 47 | 100 |
| | 25 | 40 | 100 |
| | 10 | 0 | 33 |
| 1AO | 100 | 100 | 100 |
| | 50 | 100 | 100 |
| | 25 | 100 | 100 |
| | 10 | 90 | 100 |
| | 5 | 0 | 47 |
| | 2.5 | 0 | 27 |
| 1AP | 100 | 100 | 100 |
| | 50 | 100 | 100 |
| | 25 | 93 | 100 |
| | 10 | 76 | 100 |
| | 5 | 33 | 93 |
| | 2.5 | 33 | 100 |
| | 1 | 0 | 7 |
| 1AQ | 100 | 86 | 100 |
| | 50 | 53 | 100 |
| | 25 | 13 | 86 |
| 1AS | 100 | 100 | 100 |
| | 50 | 100 | 100 |
| | 25 | 60 | 100 |
| | 10 | 7 | 60 |
| 1AT | 100 | 100 | 100 |
| | 50 | 93 | 100 |
| | 25 | 86 | 100 |
| | 10 | 43 | 100 |
| | 5 | 0 | 80 |
| | 2.5 | 0 | 7 |
| | 1 | 0 | 13 |
| 1AU | 100 | 93 | 100 |
| | 50 | 100 | 100 |
| | 25 | 100 | 100 |
| | 10 | 93 | 100 |
| | 5 | 13 | 100 |
| | 2.5 | 20 | 100 |
| | 1 | 0 | 27 |
| 1AV | 100 | 100 | 100 |
| | 50 | 100 | 100 |
| | 25 | 100 | 100 |
| | 10 | 96 | 100 |
| | 5 | 93 | 100 |
| | 2.5 | 80 | 100 |
| | 1 | 0 | 92 |

*indicates no reading taken

EXPERIMENT 3

Several of the novel compounds of this invention were tested for their efficacy as an insect molt inhibitor to prevent the emergence of the adult Mexican bean beetle (*Epilachna varivestis*).

In this test, 10-day-old bean plants were used and the test organism was the Mexican bean beetle, late third-instar larvae.

Formulation of the test compounds was accomplished in the same manner as described in Experiment 2, supra.

Two 4-inch square pots of 10-day-old bean plants, each pot containing 6 to 10 plants, were used for each concentration of each test compound solution, for the solvent, and for untreated plants. The plants were sprayed and then allowed to dry. Six leaves were removed from each pot and the cut ends were wrapped in water-soaked cellucotton. The leaves were divided between three 100×20 mm. plastic petri dishes. Three third-instar Mexican bean beetle larvae were placed in each dish. The dishes were maintained in a room with controlled temperature and humidity (as described in Experiment 1), and observed daily. New bean leaves from the original treated and untreated plants were added to the dishes as needed. The larvae were maintained and provided with treated or untreated foliage, as the case might be, until they pupated (3-5 days). The pupae were removed from the dishes and placed in clean 100×20 mm. plastic petri dishes.

After seven to ten days, the number of adult Mexican bean beetles which had emerged from the pupae were counted, and the percent adult control was determined using the following formula:

$$\% \text{ Adult Control} = \frac{\text{No. of survivors in untreated control} - \text{No. of survivors in treatment} \times 100}{\text{No. survivors in untreated control}}$$

Table 3

| Adult Mexican Bean Beetle Control | | |
|---|---|---|
| Compound | Appln. Rate ppm. | Percent Control |
| 1 | 100 | 100 |
| | 50 | 46 |
| | 25 | 37 |
| 1G | 100 | 100 |
| | 50 | 50 |
| | 25 | 0 |
| 1J | 100 | 100 |
| | 50 | 100 |

Table 3-continued

| Adult Mexican Bean Beetle Control | | |
|---|---|---|
| Compound | Appln. Rate ppm. | Percent Control |
|  | 25 | 100 |
|  | 20 | 100 |
|  | 10 | 55 |
|  | 5 | 0 |
| 1M | 100 | 36 |
|  | 50 | 28 |
|  | 25 | 36 |
| 1N | 100 | 55 |
|  | 50 | 36 |
|  | 25 | 55 |
| 1O | 100 | 100 |
|  | 50 | 100 |
|  | 25 | 100 |
|  | 10 | 14 |
|  | 5 | 25 |
|  | 1 | 0 |
| 1Q | 100 | 100 |
|  | 50 | 100 |
|  | 25 | 100 |
| 1U | 100 | 100 |
|  | 50 | 100 |
|  | 25 | 100 |
| 1V | 1000 | 87 |
|  | 100 | 0 |
| 1W | 100 | 100 |
|  | 50 | 100 |
|  | 25 | 100 |
| 1Y | 100 | 25 |
|  | 50 | 0 |
|  | 25 | 0 |

EXPERIMENT 4

Several of the novel compounds of this invention were tested for their efficacy as insecticides against the black blowfly, Phormia regina, of the order of Diptera.

Each test compound was formulated by dissolving 4 mg. of the compounds in 0.4 ml. of acetone and mixing with 40 g. of homogenized beef liver to give a 100 ppm. mixture. The liver was prepared by trimming off excess fat and connective tissue and homogenizing the liver in a blender.

Lower rates of the test compounds were prepared in an analogous manner, using smaller weights of each test compound. Thus, 1 mg. of compound in 0.4 ml. acetone, mixed with 40 g. of the homogenized beef liver gave a 25 ppm. mixture. Still lower rates were prepared as follows: 5 mg. of a test compound was dissolved in 0.5 ml. of acetone to give solution A. A 0.1 ml. portion of this solution was then diluted to 1 ml. with acetone (to give solution B), and 0.4 ml. of the resulting solution B was mixed with 40 g. of the homogenized beef liver to give a 10 ppm. mixture. Then 0.1 ml. of solution B was diluted to 1.0 ml. with acetone to give solution C. Solution C, 0.4 ml., was mixed with 40 g. of the homogenized beef liver to give a 1 ppm. mixture.

Hot drink cups, 8 oz. size, were filled one-third full of ab-sorb-dri (small animal bedding). The treated liver was divided between two cups and infested with 20, 2-day-old blowfly larvae. The infested liver was covered with more ab-sorb-dri and the cups were capped with a perforated lid. A solvent control and a treated control were prepared as follows:

A cup containing liver mixed with the solvent, that is acetone, and a cup containing liver to which no compound and no solvent were added, were also prepared to serve as a solvent control and an untreated control. Each of these cups was infested with 20, 2-day-old blowfly larvae. The infested liver was covered with more ab-sorb-dri, and the cups were capped with a perforated lid. All the cups, treated and control, were maintained in a room under controlled conditions of temperature and humidity (as described in Experiment 1) until the control larvae pupated. All the pupae were removed and placed in 100×200 mm. plastic petri dishes and held until adult flies emerged.

The number of pupae per cup was recorded at the time the pupae were placed in the petri dishes. The number of emerged adults per dish was recorded and the percent adult control was calculated in the same manner and according to the same formula as used in Experiment 3.

The test results are recorded in Table 4, which follows. In the table, column 1 identifies the test compounds; columns 2 to 5 give the percent adult control accomplished at the indicated application rates.

Table 4

| Blowfly Larvicide Test Percent Adult Control | | | | |
|---|---|---|---|---|
| Compound | 100 ppm | 25 ppm | 10 ppm | 5 ppm |
| 1 | 100 | —* | 0 | — |
| 1A | 26 | — | 0 | — |
| 1G | 97 | — | — | — |
| 1J | 100 | 100 | 25 | 0 |
| 1O | 50 | — | 0 | — |
| 1Q | 50 | — | — | — |
| 1AH | 100 | 100 | 62 | — |
| 1AL | 100 | 50 | 23 | — |

*indicates no reading taken

EXPERIMENT 5

Several of the novel compounds of this invention were tested for their efficacy as insecticides against the yellow fever mosquito, Aedes aegypti, of the order of Diptera.

Each test compound was formulated by dissolving 10 mg. of the compound in 1 ml. of acetone and mixing with 99 ml. of water to give a concentration of 100 ppm of the compound in the test solution. The lower concentrations of test solutions needed were then obtained by serial dilution of the 100 ppm solution with water. These test solutions were then placed in 100 ml. glass beakers, or, alternatively, 6 oz. plastic containers, 40 ml. of test solution per beaker or container, and 2 beakers or containers per rate. Twenty to thirty, 24-hour mosquito larvae were placed in each beaker. The larvae were fed 10–20 mg. of pulverized Purina laboratory chow daily for 7 days. During this time the beakers or containers were maintained in a room in which the temperature and humidity were continuously controlled and recorded, as described in Experiment 1.

The percent mortalities of the mosquito larvae were determined after 7 days by visual observation of the number of living larvae. All the treatments were compared to solvent and nontreated controls. The results are set forth in Table 5, which follows.

In the table, column 1 identifies the compounds by the number of the preparative example; column 2, the application rate in ppm; and column 3, the percent mortality at the indicated test rates.

Table 5

| Yellow Fever Mosquito Larvicide Test | | |
|---|---|---|
| Compound | Appln. Rate ppm. | Percent Mortality |
| 1 | 100 | 100 |
|  | 50 | 100 |

Table 5-continued

| Yellow Fever Mosquito Larvicide Test | | |
|---|---|---|
| Compound | Appln. Rate ppm. | Percent Mortality |
| | 1 | 97.5 |
| | 0.1 | 0 |
| 1A | 20 | 0 |
| | 10 | 100 |
| | 1 | 0 |
| 1G | 10 | 100 |
| | 1 | 100 |
| | 0.1 | 20 |
| 1J | 25 | 100 |
| | 1 | 75 |
| | 0.1 | 0 |
| 1M | 10 | 100 |
| | 1 | 0 |
| 1N | 10 | 95 |
| | 1 | 0 |
| 1O | 10 | 100 |
| | 1 | 40 |
| | 0.1 | 0 |
| 1P | 10 | 50 |
| | 1 | 0 |
| | 0.1 | 0 |
| 1Q | 10 | 100 |
| | 1 | 100 |
| | 0.1 | 80 |
| 1U | 10 | 100 |
| | 1 | 100 |
| | 0.1 | 50 |
| 1V | 10 | 90 |
| | 1 | 90 |
| | 0.1 | 0 |
| 1W | 10 | 100 |
| | 1 | 100 |
| | 0.1 | 50 |
| Solvent | — | 0 |
| Untreated | — | 0 |

The results of the tests show that the novel compounds coming within the scope of the generic formula, supra, are active against a number of insects in the larval stage, as the insects ingest the leaves, or any other part of their normal habitat; e.g., water, manure, and the like, to which the active compounds have been applied.

I claim:

1. A compound of the formula

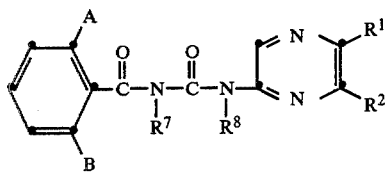

wherein

A and B are the same or different, and are halo, methyl, or trifluoromethyl;

$R^1$, when taken separately, is hydrogen, halo, $C_1$–$C_6$ alkyl, $C_3$–$C_6$ cycloalkyl, halo($C_1$–$C_4$)alkyl, nitro, cyano

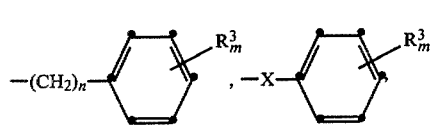

or naphthyl;

$R^2$, when taken separately, is hydrogen, halo, methyl, ethyl, cyano, or halo($C_1$–$C_2$)alkyl;

with the limitation that $R^1$ and $R^2$ may not both be hydrogen at the same time;

$R^3$ is halo, halo($C_1$–$C_4$)alkyl, $C_1$–$C_6$ alkyl, $C_1$–$C_4$ alkoxy, $C_1$–$C_4$ alkylthio, $C_1$–$C_4$ alkylsulfonyl, nitro, cyano, or phenyl;

m is 0, 1, 2, or 3;

n is 0 or 1;

X is -O-, -S-, or

and $R^7$ and $R^8$, when taken separately, are the same or different, and are hydrogen, $C_1$–$C_4$ alkanoyl, or $C_1$–$C_3$ alkoxycarbonyl.

2. The compound as in claim 1, said compound being 1-(2,6-dichlorobenzoyl)-3-(6-methyl-5-phenyl-2-pyrazinyl)urea.

3. The compound as in claim 1, said compound being 1-(2,6-dichlorobenzoyl)-3-[6-methyl-5-(4-bromophenyl)-2-pyrazinyl]urea.

4. The compound as in claim 1, said compound being 1-(2,6-dichlorobenzoyl-3-[6-methyl-5-(4-chlorophenyl)-2-pyrazinyl]urea.

5. The compound as in claim 1, said compound being 1-(2,6-dichlorobenzoyl)-3-[6-methyl-5-(4-anisyl)-2-pyrazinyl]urea.

6. The compound as in claim 1, said compound being 1-[5-(4-bromophenyl)-6-ethyl-2-pyrazinyl]-3-(2,6-dichlorobenzoyl)urea.

7. The compound as in claim 1, said compound being 1-(2,6-dichlorobenzoyl)-3-[5-(2,4-xylyl)-2-pyrazinyl]urea.

8. The compound as in claim 1, said compound being 1-(5-chloro-2-pyrazinyl)-3-(2,6-dichlorobenzoyl)-urea.

9. The compound as in claim 1, said compound being 1-(6-chloro-2-pyrazinyl)-3-(2,6-dichlorobenzoyl)urea.

10. The compound as in claim 1, said compound being 1-(5-bromo-2-pyrazinyl)-3-(2,6-dichlorobenzoyl)urea.

11. The compound as in claim 1, said compound being 1-(2,6-dichlorobenzoyl)-3-[6-(trifluoromethyl)-2-pyrazinyl]urea.

12. The compound as in claim 1, said compound being 1-(2,6-dichlorobenzoyl)-3-[5-(trifluoromethyl)-2-pyrazinyl]urea.

13. The compound as in claim 1, said compound being 1-(2,6-dichlorobenzoyl)-3-[6-methyl-5-(α,α,α-trifluoro-m-tolyl)-2-pyrazinyl]urea.

14. The compound as in claim 1, said compound being 1-(2,6-dichlorobenzoyl)-3-[6-methyl-5-(α,α,α-trifluoro-p-tolyl)-2-pyrazinyl]urea.

15. The compound as in claim 1, said compound being 1-(2,6-dichlorobenzoyl)-3-[5-phenyl-6-(trifluoromethyl)-2-pyrazinyl]urea.

16. The compound as in claim 1, said compound being 1-[5-(4-bromophenyl)-6-methyl-2-pyrazinyl]-3-(2,6-difluorobenzoyl)urea.

17. The compound as in claim 1, said compound being 1-(2,6-dichlorobenzoyl)-3-[6-methyl-5-(4-methylthio)-phenyl-2-pyrazinyl]urea.

18. The compound as in claim 1, said compound being 1-[5-(3-bromophenyl)-6-methyl-2-pyrazinyl]-3-(2,6-dichlorobenzoyl)urea.

19. The compound as in claim 1, said compound being 1-[5-(4-bromophenyl)-2-pyrazinyl]-3-(2,6-dichlorobenzoyl)urea.

20. The compound as in claim 1, said compound being 1-[5-(4-bromophenyl)-6-methyl-2-pyrazinyl]-3-(2,6-dimethylbenzoyl)urea.

21. The compound as in claim 1, said compound being 1-[5-(4-bromophenyl)-6-chloro-2-pyrazinyl]-3-(2,6-dichlorobenzoyl)urea.

22. A method of controlling insects of an order selected from the group consisting of Coleoptera, Diptera, Lepidoptera, and Orthoptera, which comprises applying to the locus of the insects an insecticidal amount of a compound of claim 1.

23. The method of claim 22, wherein the compound is 1-(2,6-dichlorobenzoyl)-3-(6-methyl-5-phenyl-2-pyrazinyl)urea.

24. The method of claim 22, wherein the compound is 1-(2,6-dichlorobenzoyl)-3-[6-methyl-5-(4-bromophenyl)-2-pyrazinyl]urea.

25. The method of claim 22, wherein the compound is 1-(2,6-dichlorobenzoyl)-3-[6-methyl-5-(4-chlorophenyl)-2-pyrazinyl]urea.

26. The method of claim 22, wherein the compound is 1-(2,6-dichlorobenzoyl)-3-[6-methyl-5-(4-anisyl)-2-pyrazinyl]urea.

27. The method of claim 22, wherein the compound is 1-[5-(4-bromophenyl)-6-ethyl-2-pyrazinyl]-3-(2,6-dichlorobenzoyl)urea.

28. The method of claim 22, wherein the compound is 1-(2,6-dichlorobenzoyl)-3-[5-(2,4-xylyl)-2-pyrazinyl]urea.

29. The method of claim 22, wherein the compound is 1-(5-chloro-2-pyrazinyl)-3-(2,6-dichlorobenzoyl)urea.

30. The method of claim 22, wherein the compound is 1-(6-chloro-2-pyrazinyl)-3-(2,6-dichlorobenzoyl)urea.

31. The method of claim 22, wherein the compound is 1-(5-bromo-2-pyrazinyl)-3-(2,6-dichlorobenzoyl)urea.

32. The method of claim 22, wherein the compound is 1-(2,6-dichlorobenzoyl)-3-[6-(trifluoromethyl)-2-pyrazinyl]urea.

33. The method of claim 22, wherein the compound is 1-(2,6-dichlorobenzoyl)-3-[5-(trifluoromethyl)-2-pyrazinyl]urea.

34. The method of claim 22, wherein the compound is 1-(2,6-dichlorobenzoyl)-3-[6-methyl-5-($\alpha,\alpha,\alpha$-trifluoro-m-tolyl)-2-pyrazinyl]urea.

35. The method of claim 22, wherein the compound is 1-(2,6-dichlorobenzoyl)-3-[6-methyl-5-($\alpha,\alpha,\alpha$-trifluoro-p-tolyl)-2-pyrazinyl]urea.

36. The method of claim 22, wherein the compound is 1-(2,6-dichlorobenzoyl)-3-[5-phenyl-6-trifluoromethyl)-2-pyrazinyl]urea.

37. The method of claim 22, wherein the compound is 1-[5-(4-bromophenyl)-6-methyl-2-pyrazinyl]-3-(2,6-difluorobenzoyl)urea.

38. The method of claim 22, wherein the compound is 1-[5-(4-bromophenyl)-6-methyl-2-pyrazinyl]-3-(2,6-dimethylbenzoyl)urea.

39. The method of claim 22, wherein the compound is 1-[5-(4-bromophenyl)-6-chloro-2-pyrazinyl]-3-(2,6-dichlorobenzoyl)urea.

40. The method of claim 22, wherein the compound is 1-[5-(3-bromophenyl)-6-methyl-2-pyrazinyl]-3-(2,6-dichlorobenzoyl)urea.

* * * * *